(12) United States Patent
Sasaki

(10) Patent No.: US 9,492,059 B2
(45) Date of Patent: Nov. 15, 2016

(54) ENDOSCOPE APPARATUS, INFORMATION STORAGE DEVICE, AND IMAGE PROCESSING METHOD

(71) Applicant: OLYMPUS CORPORATION, Tokyo (JP)

(72) Inventor: Hiroshi Sasaki, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 423 days.

(21) Appl. No.: 13/925,197

(22) Filed: Jun. 24, 2013

(65) Prior Publication Data

US 2013/0286172 A1    Oct. 31, 2013

Related U.S. Application Data

(63) Continuation of application No. PCT/JP2011/079165, filed on Dec. 16, 2011.

(30) Foreign Application Priority Data

Dec. 24, 2010    (JP) .................. 2010-287943

(51) Int. Cl.
*A61B 1/00*  (2006.01)
*A61B 1/045* (2006.01)
(Continued)

(52) U.S. Cl.
CPC ....... *A61B 1/00009* (2013.01); *A61B 1/00188* (2013.01); *A61B 1/045* (2013.01);
(Continued)

(58) Field of Classification Search
CPC .......... A61B 1/00009; A61B 1/00188; A61B 1/045; A61B 1/00; G02B 23/2476; G06T 5/003; G06T 5/50; H04N 13/02

USPC .......................................................... 348/65
See application file for complete search history.

(56) References Cited

U.S. PATENT DOCUMENTS 5,392,067 A *  2/1995  Konno et al. .................. 348/72
5,879,284 A    3/1999  Tsujita
(Continued)

FOREIGN PATENT DOCUMENTS

JP    06-253191 A    9/1994
JP    10-165365 A    6/1998
(Continued)

OTHER PUBLICATIONS

International Search Report (ISR) dated Mar. 27, 2012 (and English translation thereof) issued in International Application No. PCT/JP2011/079165.

*Primary Examiner* — Shan Elahi
(74) *Attorney, Agent, or Firm* — Holtz, Holtz & Volek PC

(57) ABSTRACT

The endoscope apparatus includes an image acquisition section (image composition processing section) that acquires a captured image in a zoom observation state in time series, the zoom observation state being an observation state in which a magnification of an optical system is higher than that in a normal observation state, a defocus amount information extraction section (texture extraction section) that extracts defocus amount information from the captured image in the zoom observation state, and a defocus amount correction section (texture correction amount calculation section, texture correction section, and blending section) that corrects the captured image based on the extracted defocus amount information.

26 Claims, 18 Drawing Sheets

(51) Int. Cl.
  *G02B 23/24* (2006.01)
  *G06T 5/00* (2006.01)
  *G06T 5/50* (2006.01)
(52) U.S. Cl.
  CPC ........... *G02B23/2476* (2013.01); *G06T 5/003* (2013.01); *G06T 5/50* (2013.01); *G06T 2207/10016* (2013.01); *G06T 2207/10024* (2013.01); *G06T 2207/10068* (2013.01); *G06T 2207/10148* (2013.01); *G06T 2207/20221* (2013.01)

(56) References Cited

U.S. PATENT DOCUMENTS

| | | | |
|---|---|---|---|
| 6,144,408 A * | 11/2000 | MacLean | H04N 9/045 348/241 |
| 6,501,551 B1 * | 12/2002 | Tearney | A61B 1/00096 356/477 |
| 6,603,885 B1 | 8/2003 | Enomoto | |
| 6,635,011 B1 * | 10/2003 | Ozawa et al. | 600/178 |
| 6,856,707 B2 | 2/2005 | Enomoto | |
| 6,862,373 B2 | 3/2005 | Enomoto | |
| 6,885,801 B1 * | 4/2005 | Shankar et al. | 385/117 |
| 6,947,091 B1 * | 9/2005 | Widmann | G02B 7/102 348/240.99 |
| 2001/0047137 A1 * | 11/2001 | Moreno | A61B 5/0075 600/475 |
| 2002/0016533 A1 * | 2/2002 | Marchitto | A61B 5/0066 600/310 |
| 2003/0036751 A1 * | 2/2003 | Anderson et al. | 606/9 |
| 2003/0076410 A1 * | 4/2003 | Beutter et al. | 348/65 |
| 2003/0103212 A1 * | 6/2003 | Westphal | A61B 3/102 356/479 |
| 2004/0246604 A1 * | 12/2004 | Fiete et al. | 359/850 |
| 2005/0058352 A1 * | 3/2005 | Deliwala | 382/232 |
| 2005/0075544 A1 * | 4/2005 | Shapiro et al. | 600/300 |
| 2005/0248655 A1 * | 11/2005 | Kitamura et al. | 348/187 |
| 2006/0183993 A1 * | 8/2006 | Horn | A61B 1/00016 600/407 |
| 2006/0184037 A1 * | 8/2006 | Ince et al. | 600/476 |
| 2006/0293558 A1 * | 12/2006 | De Groen et al. | 600/101 |
| 2007/0016022 A1 * | 1/2007 | Blalock et al. | 600/437 |
| 2007/0171536 A1 * | 7/2007 | Tsukagoshi | 359/642 |
| 2007/0253531 A1 * | 11/2007 | Okuzawa | A61B 6/00 378/62 |
| 2009/0076368 A1 * | 3/2009 | Balas | 600/407 |
| 2009/0156898 A1 * | 6/2009 | Ichimura | A61B 1/00089 600/127 |
| 2009/0207412 A1 * | 8/2009 | Mahmood et al. | 356/406 |
| 2010/0081928 A1 * | 4/2010 | Hyde | A61B 5/0084 600/431 |
| 2010/0210937 A1 * | 8/2010 | Tearney | A61B 5/0066 600/424 |
| 2011/0285995 A1 * | 11/2011 | Tkaczyk | G01J 3/02 356/326 |
| 2012/0262559 A1 * | 10/2012 | On | H04N 5/23267 348/65 |
| 2013/0083180 A1 * | 4/2013 | Sasaki | H04N 5/23212 348/65 |
| 2013/0286172 A1 * | 10/2013 | Sasaki | A61B 1/00009 348/65 |

FOREIGN PATENT DOCUMENTS

| | | |
|---|---|---|
| JP | 2000-156785 A | 6/2000 |
| JP | 2003-140030 A | 5/2003 |
| JP | 2003-348377 A | 12/2003 |
| JP | 2005-309945 A | 11/2005 |
| JP | 2005-332383 A | 12/2005 |
| JP | 2008-011491 A | 1/2008 |
| JP | 2010-022772 A | 2/2010 |

\* cited by examiner

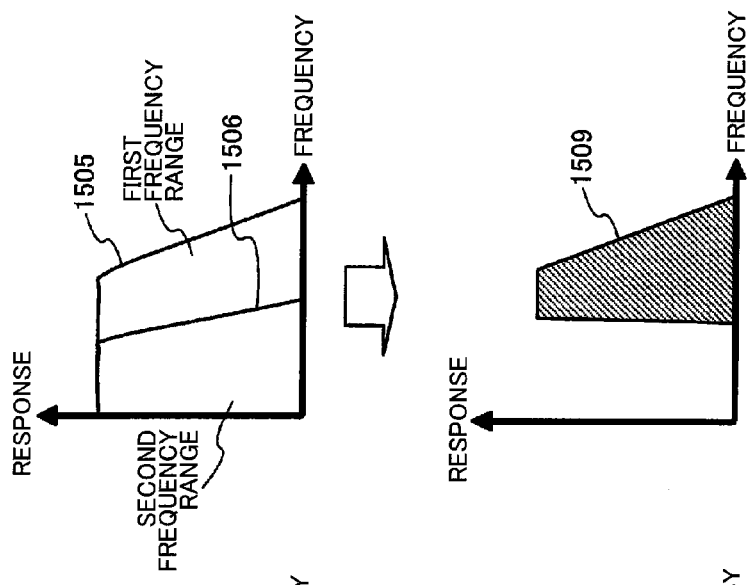
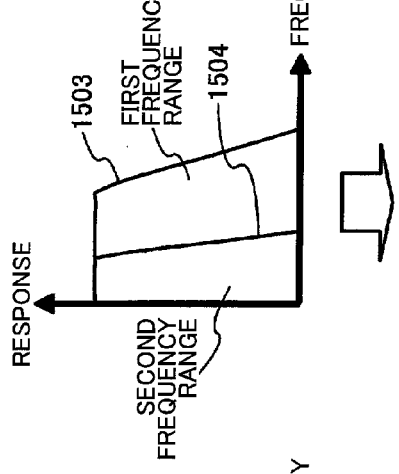
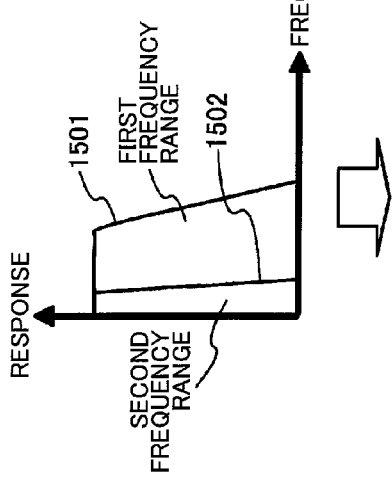

high
ENDOSCOPE APPARATUS, INFORMATION STORAGE DEVICE, AND IMAGE PROCESSING METHOD

CROSS REFERENCE TO RELATED APPLICATION

This application is a continuation of International Patent Application No. PCT/JP2011/079165, having an international filing date of Dec. 16, 2011, which designated the United States, the entirety of which is incorporated herein by reference. Japanese Patent Application No. 2010-287943 filed on Dec. 24, 2010 is also incorporated herein by reference in its entirety.

BACKGROUND

The present invention relates to an endoscope apparatus, an information storage device, an image processing method, and the like.

An improvement in detection accuracy of a lesion in a body cavity has been desired in the field of endoscopic diagnosis. An endoscope that includes a zoom optical system that improves the detection accuracy by magnifying the difference in tissue between a lesion area and a normal area at a magnification almost equal to that of a microscope (hereinafter may be appropriately referred to as "zoom endoscope") has been known.

A zoom endoscope may be configured to achieve a magnification of several ten to several hundred times. The fine structure of the mucosal surface layer and the blood vessel distribution pattern can be observed by utilizing such a zoom endoscope in combination with a stain solution or a blood vessel-enhanced (weighted) image obtained using narrow-band illumination light (hereinafter may be referred to as "NBI image"). It is known that a lesion area and a normal area differ in the above pattern, and the above pattern has been used as a diagnostic criterion for lesions.

However, the depth of field significantly decreases during zoom observation along with an increase in magnification as compared with normal observation. In this case, it is difficult to continuously position the end of the insertion section (hereinafter may be referred to as "scope" or "imaging section") of the endoscope within the in-focus range relative to the object, and considerable skill is required to continuously obtain (observe) an in-focus image.

If it takes time to position the scope during zoom observation in order to obtain an in-focus image, the entire diagnosis time necessarily increases. As a result, the doctor gets tired, and the burden imposed on the patient increases.

The above problem may be solved by the method disclosed in JP-A-10-165365 that sets an area that is considered to be outside the depth-of-field range within one image, and performs a defocus restoration process to implement an increase in depth of field. The method disclosed in JP-A-10-165365 detects distance when observing a tubular cavity using the endoscope, and performs the defocus restoration process on an area within a given distance range.

The above problem may also be solved by the method disclosed in JP-A-2003-140030 that performs an autofocus process during zoom observation.

SUMMARY

According to one aspect of the invention, there is provided an endoscope apparatus including: an image acquisition section that acquires a captured image in a zoom observation state in time series, the zoom observation state being an observation state in which a magnification of an optical system is higher than that in a normal observation state; a defocus amount information extraction section that extracts defocus amount information from the captured image in the zoom observation state; and a defocus amount correction section that corrects the captured image based on the extracted defocus amount information, the defocus amount information extraction section including a specific frequency band image extraction section that extracts a specific frequency band image from the captured image, the specific frequency band image being an image of a specific frequency band component, the specific frequency band image extraction section including a captured image amplitude calculation section that calculates an amplitude value of the captured image, and the specific frequency band image extraction section not extracting the specific frequency band image when the amplitude value calculated by the captured image amplitude calculation section is within a first amplitude range, and extracting the specific frequency band image when the amplitude value calculated by the captured image amplitude calculation section is within a second amplitude range, the second amplitude range being a range that corresponds to an amplitude value that is smaller than an amplitude value within the first amplitude range.

According to another aspect of the invention, there is provided an information storage device storing a program that instructs a computer to perform steps of:

acquiring a captured image in a zoom observation state in time series, the zoom observation state being an observation state in which a magnification of an optical system is higher than that in a normal observation state;

performing a defocus amount information extraction process that extracts defocus amount information from the captured image in the zoom observation state; and performing a defocus amount correction process that corrects the captured image based on the extracted defocus amount information, the defocus amount information extraction process calculating an amplitude value of the captured image, not performing a specific frequency band image extraction process when the calculated amplitude value is within a first amplitude range, and performing the specific frequency band image extraction process when the calculated amplitude value is within a second amplitude range, the specific frequency band image extraction process extracting a specific frequency band image from the captured image, the specific frequency band image being an image of a specific frequency band component, and the second amplitude range being a range that corresponds to an amplitude value that is smaller than an amplitude value within the first amplitude range.

According to another aspect of the invention, there is provided an image processing method comprising:

acquiring a captured image in a zoom observation state in time series, the zoom observation state being an observation state in which a magnification of an optical system is higher than that in a normal observation state;

performing a defocus amount information extraction process that extracts defocus amount information from the captured image in the zoom observation state; and performing a defocus amount correction process that corrects the captured image based on the extracted defocus amount information, the defocus amount information extraction process calculating an amplitude value of the captured image, not performing a specific frequency band image extraction process when the calculated amplitude value is within a first amplitude range, and performing the specific frequency band image extraction process when the calculated amplitude value is within a second amplitude range, the specific frequency band image extraction process extracting a specific frequency band image from the captured image, the specific frequency band image being an image of a specific frequency band component, and the second amplitude range being a range that corresponds to an amplitude value that is smaller than an amplitude value within the first amplitude range.

BRIEF DESCRIPTION OF THE DRAWINGS

FIGS. 19A to 19C are views illustrating the relationship between the observation magnification of an optical system and a frequency range to be extracted.

DESCRIPTION OF EXEMPLARY EMBODIMENTS

Figure 1:
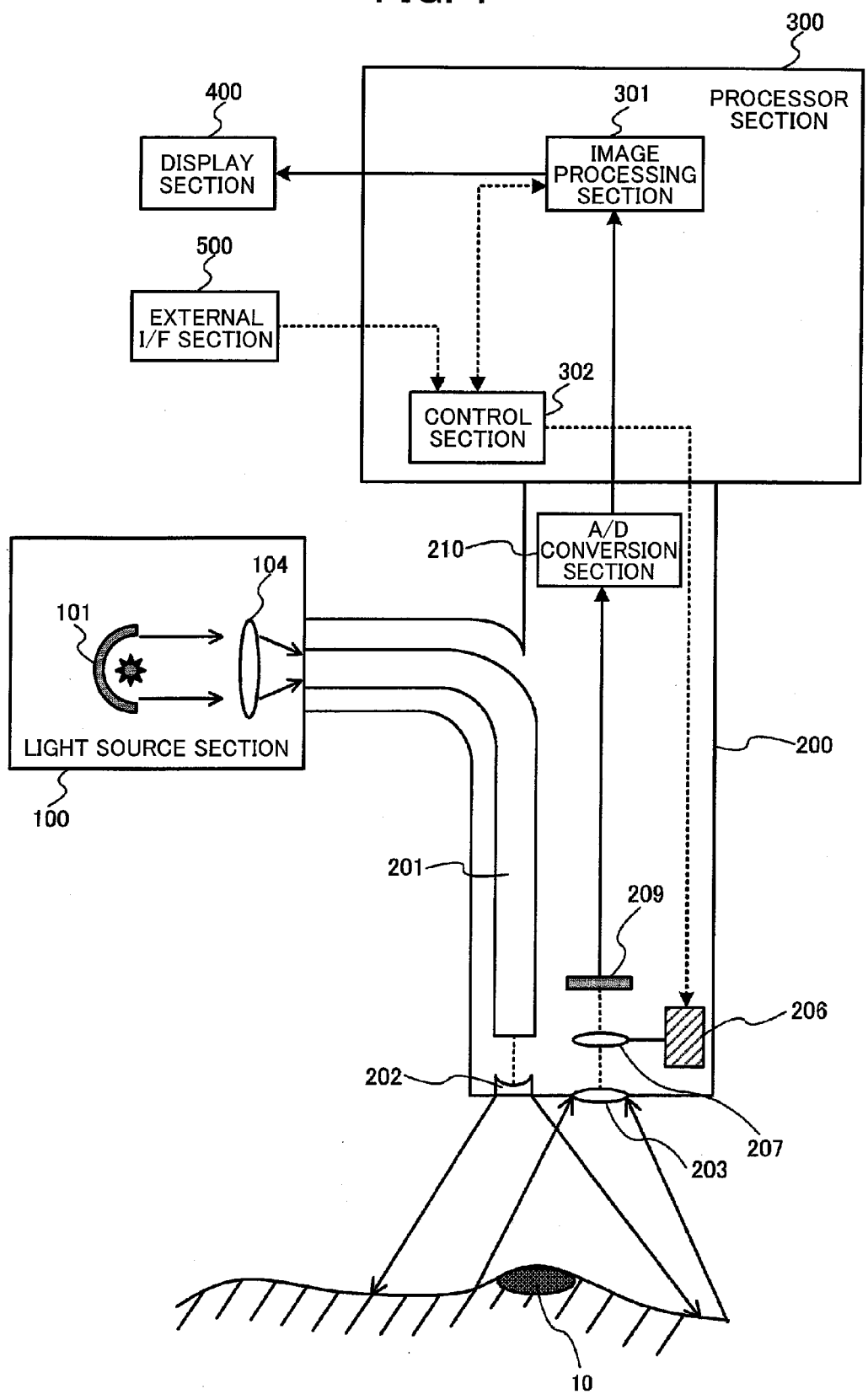
FIG. 1 illustrates a system configuration example of an endoscope apparatus according to one embodiment of the invention.

According to one embodiment of the invention, there is provided an endoscope apparatus comprising:
an image acquisition section that acquires a captured image in a zoom observation state in time series, the zoom observation state being an observation state in which a magnification of an optical system is higher than that in a normal observation state;
a defocus amount information extraction section that extracts defocus amount information from the captured image in the zoom observation state; and
a defocus amount correction section that corrects the captured image based on the extracted defocus amount information,
the defocus amount information extraction section including a specific frequency band image extraction section that extracts a specific frequency band image from the captured image, the specific frequency band image being an image of a specific frequency band component,
the specific frequency band image extraction section including a captured image amplitude calculation section that calculates an amplitude value of the captured image, and
the specific frequency band image extraction section not extracting the specific frequency band image when the amplitude value calculated by the captured image amplitude calculation section is within a first amplitude range, and extracting the specific frequency band image when the amplitude value calculated by the captured image amplitude calculation section is within a second amplitude range, the second amplitude range being a range that corresponds to an amplitude value that is smaller than an amplitude value within the first amplitude range.

According to another embodiment of the invention, there is provided an information storage device storing a program that instructs a computer to perform steps of:
acquiring a captured image in a zoom observation state in time series, the zoom observation state being an observation state in which a magnification of an optical system is higher than that in a normal observation state;
performing a defocus amount information extraction process that extracts defocus amount information from the captured image in the zoom observation state; and
performing a defocus amount correction process that corrects the captured image based on the extracted defocus amount information,
the defocus amount information extraction process calculating an amplitude value of the captured image, not performing a specific frequency band image extraction process when the calculated amplitude value is within a first amplitude range, and performing the specific frequency band image extraction process when the calculated amplitude value is within a second amplitude range, the specific frequency band image extraction process extracting a specific frequency band image from the captured image, the specific frequency band image being an image of a specific frequency band component, and the second amplitude range being a range that corresponds to an amplitude value that is smaller than an amplitude value within the first amplitude range.

According to another embodiment of the invention, there is provided an image processing method comprising:
acquiring a captured image in a zoom observation state in time series, the zoom observation state being an observation state in which a magnification of an optical system is higher than that in a normal observation state;
performing a defocus amount information extraction process that extracts defocus amount information from the captured image in the zoom observation state; and
performing a defocus amount correction process that corrects the captured image based on the extracted defocus amount information,
the defocus amount information extraction process calculating an amplitude value of the captured image, not performing a specific frequency band image extraction process when the calculated amplitude value is within a first amplitude range, and performing the specific frequency band image extraction process when the calculated amplitude value is within a second amplitude range, the specific frequency band image extraction process extracting a specific frequency band image from the captured image, the specific frequency band image being an image of a specific frequency band component, and the second amplitude range being a range that corresponds to an amplitude value that is smaller than an amplitude value within the first amplitude range.

Exemplary embodiments of the invention are described below. Note that the following exemplary embodiments do not in any way limit the scope of the invention laid out in the claims. Note also that all of the elements described in connection with the following exemplary embodiments should not necessarily be taken as essential elements of the invention.

1. Method

A method employed in several embodiments of the invention is described below. The method employed in several embodiments of the invention makes it possible to acquire an image for which the defocus amount is reduced to achieve an in-focus state without increasing the amount of noise.

It is difficult to acquire an in-focus image in a zoom observation mode that utilizes a magnification of several ten to several hundred times since the depth of field significantly decreases. In order to deal with this problem, an image for which the defocus amount is reduced to achieve an in-focus state is acquired by performing a defocus restoration process implemented by image processing on a defocused image.

The details of the method employed in several embodiments of the invention are described below. A defocused image may be acquired by an image acquisition section (image composition processing section 310) during zoom observation since it is difficult to achieve an in-focus state. In this case, an area that shows a small change in grayscale (e.g., the surface of the mucous membrane or the blood vessel structure) is significantly affected by the defocused state, and an area that shows a large change in grayscale (e.g., folds) is affected by the defocused state to only a small extent. Specifically, the amplitude of an image of a fine structure (e.g., mucous membrane or blood vessel) is significantly reduced by the defocused state. Therefore, an image of a fine structure (e.g., mucous membrane or blood vessel) (hereinafter may be referred to as "texture image" or "specific frequency band image") is extracted from the captured image.

A correction process that increases the reduced amplitude value (e.g., amplifies the signal value) is performed on the extracted texture image. The captured image (defocused image) acquired by the image acquisition section and the texture image subjected to the correction process are blended to acquire an image that has been corrected so that the texture that is useful for diagnosis is in focus. According to the above method, since the defocus restoration process is performed on an area that is significantly affected by the defocused state, but is not performed on an area that is affected by the defocused state to only a small extent, a noise component, and the like, it is possible to acquire a defocus-corrected image that does not produce a wrong visual impression. Specifically, it is possible to acquire an image in which the defocus restoration process is intensively performed on the texture that is useful for diagnosis.

A first embodiment illustrates a method that extracts the texture image using a two-stage bilateral filter. In this case, it is necessary to extract an image of the surface of the mucous membrane, blood vessels, and the like so that folds and the like are excluded. Therefore, a filter that has frequency characteristics (e.g., high-pass frequency characteristics or band-pass frequency characteristics) and amplitude characteristics is applied. The amplitude is determined from the pixel value of an attention pixel and the pixel value of its peripheral pixel. Folds have a large amplitude value, and the mucous membrane, blood vessels, and the like have a small amplitude value. Note that it suffices that an image be acquired that has an amplitude value corresponding to a small to very small amplitude, and is within a specific frequency range. The filter used to acquire such an image is not limited to a bilateral filter.

Figure 14A:
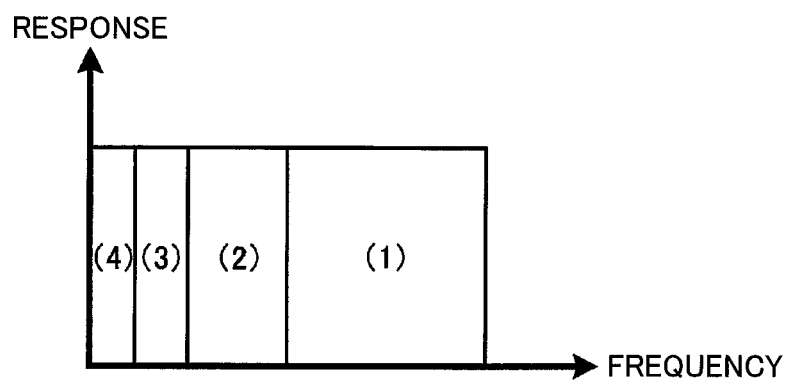
FIGS. 14A and 14B are views illustrating sub-band image division examples.
Figure 14B:
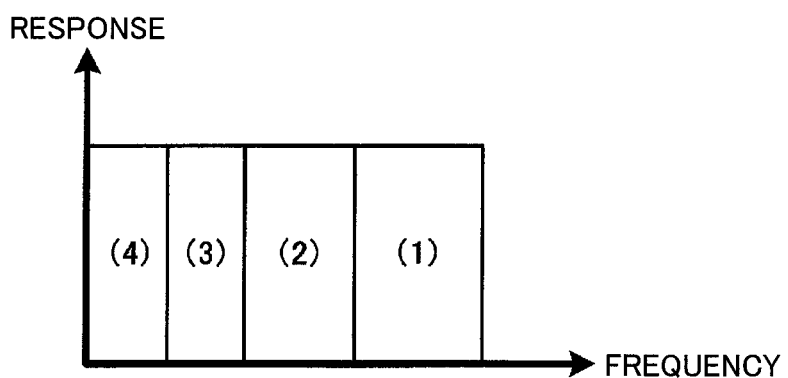

A second embodiment illustrates an example in which the texture image is extracted using a sub-band image (see FIGS. 14A and 14B). The second embodiment is characterized in that an image for which the defocus amount is reduced is acquired by performing an optical autofocus process in addition to the defocus restoration process implemented by image processing.

2. First Embodiment 2.1 Configuration

FIG. 1 is a block diagram illustrating the entire configuration of an endoscope apparatus according to the first embodiment. The endoscope apparatus according to the first embodiment includes a light source section 100, an imaging section 200, a processor section 300, a display section 400, and an external I/F section 500.

The light source section 100 includes a white light source 101, and a condenser lens 104 that focuses illumination light emitted from the white light source 101 on the incident end face of a light guide fiber 201.

The imaging section 200 is formed to be elongated and flexible (i.e., can be curved) so that the imaging section 200 can be inserted into a body cavity or the like. The imaging section 200 includes the light guide fiber 201 that guides the light focused by the light source section 100, an illumination lens 202 that diffuses the light that has been guided by the light guide fiber 201, and applies the diffused light to the observation target, an objective lens 203 that focuses reflected light from the observation target, an in-focus distance control section 206, an in-focus distance adjustment lens 207, an image sensor 209 that detects the focused light, and an A/D conversion section 210 that converts a photo-electrically converted analog signal output from the image sensor 209 into a digital signal. The image sensor 209 is a single-chip image sensor (complementary color or primary color) in which color filters are disposed in the pixels in a given array. A CCD sensor, a CMOS sensor, or the like may be used as the image sensor 209.

The processor section 300 includes an image processing section 301 and a control section 302. The display section 400 is a display (e.g., CRT or liquid crystal monitor) that can display a moving image.

The external I/F section 500 is an interface that allows the user to perform an input operation or the like on the endoscope apparatus. The external I/F section 500 includes a power switch (power ON/OFF switch), a shutter button for starting an imaging operation, a mode (e.g., imaging mode) switch knob (e.g., the in-focus distance adjustment lens is moved by moving a zoom lever illustrated in FIG. 6 so that the observation mode is set to a zoom observation mode to obtain an in-focus state at a closer position), and the like. The external I/F section 500 outputs the input information to the control section 302.

The relationship between the in-focus distance control section 206 included in the imaging section 200, the in-focus distance adjustment lens 207 included in the imaging section 200, and the control section 302 is described in detail below. The endoscope apparatus according to the first embodiment can implement two observation modes that differ in observation magnification.

The two observation modes include a normal observation mode and a zoom observation mode. In the normal observation mode, screening examination is mainly performed using a deep-focus wide-field image. In the zoom observation mode, the mucous membrane structure, the blood vessel distribution, and the like in the lesion area found by screening examination are magnified to determine whether or not the lesion area is malignant.

In order to switch the observation mode between the normal observation mode and the zoom observation mode, the control section 302 transmits an in-focus distance adjustment control signal to the in-focus distance control section 206 based on an operation performed on the zoom lever (see FIG. 6) of the external I/F section 500. The in-focus distance control section 206 controls the movement of the in-focus distance adjustment lens 207 based on the received in-focus distance adjustment control signal.

The details of the control process performed by the in-focus distance control section 206 and the operation performed by the user in the zoom observation mode are described below.

When the zoom observation mode has been selected, the in-focus distance adjustment lens 207 is moved via the in-focus distance control section 206 so that a predetermined in-focus distance that achieves a close in-focus state is implemented. In order to implement a smooth transition to zoom observation, the scope is moved toward the observation target as close as possible in the normal observation mode while maintaining an in-focus state, for example. The user then switches the observation mode to the zoom observation mode by operating the zoom lever of the external I/F section 500. The user changes the magnification continuously (or stepwise) by operating the zoom lever, and gradually moves the scope closer to the observation target (since the depth of field decreases) to bring the observation target into focus. The desired magnification and an in-focus state can be achieved by performing the above operation.

Specifically, a defocused image is obtained unless the user performs a skilled operation that finely moves the end of the scope closer to the observation target as the magnification increases. It is very difficult to continuously capture the observation target within the screen in an in-focus state during zoom observation.

When the normal observation mode has been selected, the in-focus distance adjustment lens 207 is moved via the in-focus distance control section 206 so that an in-focus distance that achieves an angle of view and a depth of field sufficient to perform screening examination is implemented. In this case, the user can observe the observation target by merely moving the end of the scope toward the observation target since an in-focus state is always achieved. Therefore, the user need not perform a complex and fine operation.

The details of the image processing section 301 included in the processor section 300 are described below with reference to FIG. 2 (block diagram).

The image processing section 301 includes an image composition processing section 310, a texture extraction section 320, a texture correction amount calculation section 340, a texture correction section 360, and a blending section 370.

The flow of data transferred between these sections is described below. The time-series captured image output from the A/D conversion section 210 is input to the image composition processing section 310. The control section 302 is connected to the image composition processing section 310, and process parameters (e.g., OB clamp value, WB coefficient, color correction coefficient, grayscale transformation table, and edge enhancement level) that are stored in the control section 302 in advance are input to the image composition processing section 310. The image composition processing section 310 generates a time-series display image that can be observed on the display from the input time-series captured image based on the process parameters, and outputs the time-series display image to the texture extraction section 320 and the blending section 370.

The texture extraction section 320 receives the time-series display image output from the image composition processing section 310. The texture extraction section 320 also receives an observation mode signal (i.e., information that indicates the zoom observation mode or the normal observation mode) designated by the user using the external I/F section 500 and magnification information about the imaging section 200 from the control section 302. The texture extraction section 320 starts operation when the observation mode has been set to the zoom observation mode, and extracts a texture image from the input time-series display image (each frame). The texture image is an image that shows a small change in grayscale and corresponds to the fine mucous membrane structure, blood vessels, and the like in the surface of tissue (i.e., observation target). An area in which the illumination light is specularly reflected by the mucosal surface layer, and an area that shows a large change in grayscale (e.g., folds) are excluded from the texture image as much as possible. The details of the texture extraction section 320 are described later.

Figure 18:
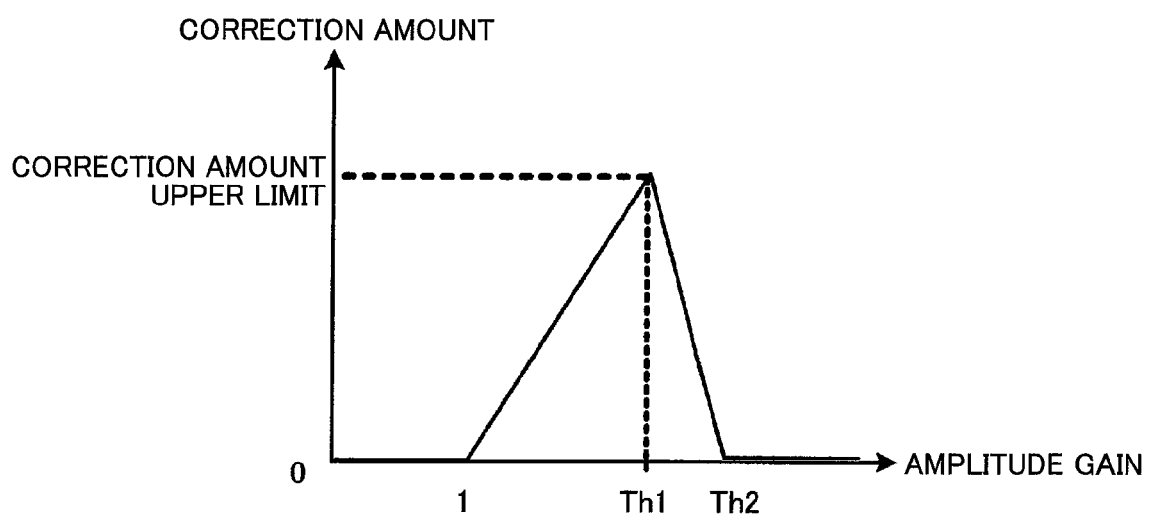
FIG. 18 is a view illustrating the relationship between an amplitude gain and a correction amount.

The texture image extracted by the texture extraction section 320 is input to the texture correction amount calculation section 340, and the texture correction amount calculation section 340 calculates the correction amount for the texture image based on the observation mode signal output from the control section 302, a texture reference threshold value, and the amplitude value of the texture image. The calculated correction amount is output to the texture correction section 360. Note that the term "texture reference threshold value" used herein refers to a determination threshold value for selecting a reference amplitude value from the amplitude values of a plurality of texture images calculated by the texture correction amount calculation section 340 in time series. The correction amount is calculated based on an amplitude gain at which the amplitude value of the currently extracted texture image is equal to the reference amplitude value. When the amplitude gain is equal to or larger than a given threshold value, it is determined that significant information is not included in the extracted texture image (i.e., the extracted texture image is defocused), and the correction amount is set to 0. As illustrated in FIG. 18, two threshold values Th1 and Th2 may be set to the amplitude gain, and the correction amount may be gradually and continuously changed between the threshold values Th1 and Th2. The details of the texture correction amount calculation section 340 are described later.

The texture correction section 360 multiplies the texture image by the correction amount to generate a corrected texture image, and outputs the corrected texture image to the blending section 370.

The blending section 370 receives the time-series display image output from the image composition processing section 310, and the corrected texture image output from texture correction section 360 and corresponding to the time-series display image, and sums the time-series display image and the corrected texture image when the observation mode signal output from the control section 302 indicates the zoom observation mode to generate a defocus-corrected image.

The defocus-corrected image is output to the display section 400, and displayed on the display section 400. When the observation mode is the normal observation mode, the time-series display image is output directly to the display section 400 without being summed with the corrected texture image.

2.2 Detailed Configuration of Defocus Amount Information Extraction Section

The details of a defocus amount information extraction section are described below. The defocus amount information extraction section corresponds to the texture extraction section 320 illustrated in FIG. 2.

The details of the texture extraction section 320 are described below with reference to FIG. 3 (block diagram). The texture extraction section 320 includes an area extraction section 321, a filter coefficient calculation section 322, a filtering section 323, a noise amount estimation section 324, a subtraction section 325, an area extraction section 326, a filter coefficient calculation section 327, a filtering section 328, and a filter parameter control section 329.

The flow of data transferred between these sections is described below. The observation mode signal and the magnification information output from the control section 302 are input to the filter parameter control section 329, and converted into a filter coefficient generation parameter. The filter coefficient generation parameter is output to the filter coefficient calculation section 322 and the noise amount estimation section 324.

The time-series display image output from the image composition processing section 310 is input to the area extraction section 321. An attention pixel and a p×q pixel area (p and q are arbitrary positive integers) around the attention pixel are extracted from the time-series display image, and output to the filter coefficient calculation section 322 and the filtering section 323. The time at which the time-series display image has been captured is referred to as t, the pixel value at three-dimensional coordinates (two-dimensional coordinates=(x, y)) is referred to as P(x, y, t), and the three-dimensional coordinates of the attention pixel subjected to the filter process are referred to as (x0, y0, t). The time-series display image is a color image, and the pixel value P(x, y, t) is a three-dimensional vector that includes three (R, G, and B) channels.

The filter coefficient calculation section 322 calculates the filter coefficient based on the filter coefficient generation parameter output from the filter parameter control section 329. The filter coefficient generation parameter input to the filter coefficient calculation section 322 is a quantity for converting the absolute value of the difference in pixel value between the attention pixel and the peripheral pixel(s) (p×q pixel area) into the filter coefficient. For example, when using a bilateral filter that utilizes a product of two Gaussian functions (see expression (1)), an index value $\sigma 1s$ for the absolute value of the difference in pixel value between the attention pixel and the peripheral pixel(s) is the filter coefficient generation parameter.

A filter coefficient F1(x, y, t) is shown by the following expression (1). $\Sigma xy$ is the total pixel value of the p×q pixel area, and Pf(x0, y0, t) is the pixel value obtained by the filter process.

$$F_1(x,y,t)=\exp(-\{(x-x_0)^2+(y-y_0)^2\}/\{2*\sigma_d^2\})* \\ \exp(-|P(x,y,t)-P(x_0,y_0,t)|^2/\{2*\sigma_{1s}^2\}) \quad (1)$$

The filtering section 323 performs the filter process using the pixel value P(x, y, t) of the p×q pixel area output from the area extraction section 321 and the filter coefficient F1(x, y, t) output from the filter coefficient calculation section 322, and calculates the pixel value Pf(x0, y0, t) (i.e., the pixel value obtained by the filter process) using the following expression (2). The calculation result is output to the subtraction section 325 and the noise amount estimation section 324.

$$P_f(x_0,y_0,t)=\Sigma_{xy}P(x,y,t)*F_1(x,y,t)/\Sigma_{xy}F_1(x,y,t) \quad (2)$$

The subtraction section 325 receives the pixel value P(x0, y0, t) of the time-series display image output from the image composition processing section 310 and the pixel value Pf(x0, y0, t) (obtained by the filter process) output from the filtering section 323, subtracts the pixel value Pf(x0, y0, t) from the pixel value P(x0, y0, t) to calculate a differential value D(x0, y0, t), and temporarily stores a differential image indicated by the calculated differential value D(x0, y0, t). The differential image thus stored is output to the area extraction section 326.

The noise amount estimation section 324 receives a noise amount estimation model (i.e., a function that converts a pixel value into a noise amount) output from the filter parameter control section 329 as the filter coefficient generation parameter, and the pixel value Pf(x0, y0, t) (obtained by the filter process) output from the filtering section 323, and estimates a noise amount N(x0, y0, t) corresponding to the pixel value Pf(x0, y0, t). The estimated noise amount N(x0, y0, t) is output to the filter coefficient calculation section 327.

The noise amount estimation model is determined by capturing a gray chart having a plurality of reflectances that achieve uniform brightness within a given area, and calculating the average value and the standard deviation $\sigma$ of the pixel values P(x, y, t) of the time-series display image output from the image composition processing section 310 within the given area (within the gray chart). A more detailed relationship between each pixel value and the noise amount (e.g., the standard deviation is used as the noise amount) within the domain is calculated from the average values and the standard deviation using a function fitted by a polynomial approximation curve, and the function is subjected to broken line approximation, or a look-up table is generated using the function, for example.

The area extraction section 326 extracts a v×w pixel area (v and w are arbitrary positive integers) around the attention pixel from the differential image output from the subtraction section 325, and outputs the extracted v×w pixel area to the filter coefficient calculation section 327 and the filtering section 328.

The filter coefficient calculation section 327 calculates the filter coefficient based on the absolute value of the difference between the attention differential pixel value D (x0, y0, t) and the peripheral differential pixel value D(x, y, t) in the v×w pixel area based on the noise amount N(x0, y0, t) output from the noise amount estimation section 324. The noise amount N(x0, y0, t) controls conversion into the filter coefficient. An index value $\sigma 2s$ for the absolute value of the difference between the attention differential pixel value and the peripheral differential pixel value is linked to the noise amount N(x0, y0, t) as indicated by the following expression (3) (bilateral filter).

$$F_2(x,y,t)=\exp(-\{(x-x_0)^2+(y-y_0)^2\}/\{2*\sigma_d^2\})* \\ \exp(-|D(x,y,t)-D(x_0,y_0,t)|^2/\{2*\sigma_{2s}^2\})$$

$$\sigma_{2s}\alpha*N(x_0,y_0,t) \quad \alpha \text{ is an arbitrary coefficient} \quad (3)$$

The filtering section 328 performs the filter process using the differential pixel value D(x, y, t) of the v×w pixel area output from the area extraction section 326 and the filter coefficient F2(x, y, t) output from the filter coefficient calculation section 327, and calculates the differential pixel value Df(x0, y0, t) (i.e., the differential pixel value obtained by the filter process) using the following expression (4). The calculation result is output to the texture correction amount calculation section 340.

$$D_f(x_0,y_0,t)=\Sigma_{x,y}D(x,y,t)*F_2(x,y,t)/\Sigma_{x,y}F_2(x,y,t) \quad (4)$$

The concept of the characteristics of the bilateral filters F1(x, y, t) and F2(x, y, t) and the texture extraction process is described below with reference to FIGS. 4A to 4C.

The index value σ1s that controls the filter coefficient of the filter F1(x, y, t) is set to be sufficiently larger than the index value σ2s for the filter F2(x, y, t).

The filter F1(x, y, t) has strong low-pass frequency characteristics (see 804 in FIG. 4B) in a region in which the difference in pixel value |P(x, y, t)−P(x0, y0, t)| or the difference in differential pixel value |D(x, y, t)−D(x0, y0, t)| (second term) that mainly determines the filter coefficient is equal to or less than the index value σ1s and is larger than the index value σ2s. The filter F2(x, y, t) has weak low-pass frequency characteristics (see 803 in FIG. 4B). Therefore, a large difference in filter characteristics occurs.

The filter F1(x, y, t) has weak low-pass frequency characteristics (see 802 in FIG. 4A), and the filter F2(x, y, t) has weaker low-pass frequency characteristics (see 801 in FIG. 4A) in a region in which the difference in pixel value is larger than the above difference in pixel value. In this case, the difference in filter characteristics is small.

The filter F1(x, y, t) has strong low-pass frequency characteristics (see 806 in FIG. 4C) in a region in which the difference in pixel value is smaller than the index value σ2s. The filter F2(x, y, t) also has strong low-pass frequency characteristics (see 805 in FIG. 4C). In this case, the difference in filter characteristics is also small.

The texture in an area having a given small difference in pixel value is extracted by utilizing the difference in frequency characteristics caused by the difference in pixel value (amplitude value) of the two bilateral filters.

Specifically, the frequency band of the differential image output from the subtraction section 325 has high-pass characteristics other than the frequency characteristics indicated by 804 in the texture area in which the difference in pixel value is small. Since only a high frequency is blocked by the filtering section 328 (see the frequency characteristics indicated by 803), the signal output from the filtering section 328 has wide band-pass frequency characteristic between the frequency characteristics indicated by 803 and the frequency characteristics indicated by 804. The desired texture can be extracted by adjusting the above characteristics to the frequency band of the mucous membrane structure or the blood vessel distribution pattern (i.e., observation target).

The band of the signal output from the subtraction section 325 has high-pass characteristics other than the frequency characteristics indicated by 802 in the specular reflection area or the edge structure (e.g., folds) in which the difference in pixel value is large. Since a high frequency is blocked by the filtering section 328 due to the frequency characteristics indicated by 801, the signal output from the filtering section 328 has a small passband, and the specular reflection area or a large edge structure (e.g., folds) can be blocked.

Since a difference in filter characteristics occurs to only a small extent (see FIG. 4C) for a noise component that is present in a region in which a change in pixel value is very small (a change due to the noise amount is sufficiently smaller than a change in pixel value in the texture area), the signal output from the filtering section 328 has a small passband, and the noise component can be blocked.

As a result, only the texture image having a small difference in pixel value is output from the texture extraction section 320. The frequency characteristics and the amplitude characteristics of the extraction target texture image can be controlled using the index values σ1s and σ2s.

The filter parameter control section 329 can control the index values σ1s and σ2s by inputting the magnification information to the filter parameter control section 329 via the control section 302 when the zoom lever of the external I/F section 500 is operated, and the magnification of the time-series display image is changed continuously (stepwise), and the tissue structure corresponding to each magnification can be more accurately extracted as the texture image.

For example, the index values σ1s and σ2s are set to a large value (σ1s>σ2s) when the magnification is low (see FIG. 19A) so that the filters F1 and F2 respectively have frequency characteristics indicated by 1502 and 1501 to extract a low-frequency band 1507 as the texture image. The index values σ1s and σ2s are set to a value (σ1s>σ2s) smaller than that when the magnification is low when the magnification is medium (see FIG. 19B) so that the filters F1 and F2 respectively have frequency characteristics indicated by 1504 and 1503 to extract a medium-frequency band 1508 as the texture image. The index values σ1s and σ2s are set to a value (σ1s>σ2s) smaller than that when the magnification is medium when the magnification is high (see FIG. 19C) so that the filters F1 and F2 respectively have frequency characteristics indicated by 1506 and 1505 to extract a high-frequency band 1509 as the texture image.

The frequency band of the extraction target texture image is changed corresponding to the magnification as described above because a large reddened or faded area that shows a subtle change in color is important when the magnification is low, the structure of the gland duct and the blood vessel distribution pattern are important when the magnification is medium, and the structure of the fine pit pattern and the fine blood vessels in the mucosal surface layer are important when the magnification is high.

2.3 Detailed Configuration of Defocus Amount Correction Section

A defocus amount correction section is described below. The defocus amount correction section corresponds to the texture correction amount calculation section 340, the texture correction section 360, and the blending section 370.

The texture correction amount calculation section 340 is described below with reference to FIG. 5 (block diagram). The texture correction amount calculation section 340 includes an amplitude calculation section 341, a reference amplitude update determination section 342, a reference amplitude storage section 343, a correction amount calculation section 344, and a correction amount control section 345.

The flow of data transferred between these sections is described below. The correction amount control section 345 receives the observation mode signal, the texture reference threshold value, and the correction amount upper limit output from the control section 302 and the current reference amplitude value output from the reference amplitude storage section 343. The correction amount control section 345 sets the reference amplitude determination threshold value based on the observation mode signal, the texture reference threshold value, and the reference amplitude value, outputs the reference amplitude determination threshold value to the reference amplitude update determination section 342, and outputs the correction amount upper limit to the correction amount calculation section 344.

The texture reference threshold value is a reference value for determining whether or not the captured time-series display image is defocused, and varies depending on the imaging performance. Therefore, a different texture reference threshold value is set corresponding to the type of scope. The reference value is stored in a ROM (not illustrated in the drawings) that is included in the imaging section 200, and the reference value is input to the control section 302 of the processor section 300 when the imaging section 200 has been connected to the processor section 300. When the amplitude value of the texture image is smaller than the texture reference threshold value, it is determined that it is impossible to successfully implement the defocus restoration process since the degree of defocus is high.

The reference amplitude value is the correction target value. A defocused state is basically corrected by performing a correction process that causes the amplitude value of the texture image to be equal to the reference amplitude value. Note that an exceptional correction process may also be performed. The details of the correction process are described later.

The reference amplitude value determination threshold value is a threshold value for selecting the reference amplitude value. The reference amplitude value determination threshold value is set to the texture reference threshold value when the observation mode signal has changed to the zoom observation mode, otherwise it is set to the average value of the texture reference threshold value and the reference amplitude value, for example. A state in which the amplitude value of the texture image exceeds the reference amplitude value determination threshold value is used as a condition whereby the reference amplitude value is updated.

The amplitude calculation section 341 calculates the amplitude value MA(t) of the texture image extracted at the time t and output from the texture extraction section 320. The amplitude value may be defined by the maximum value of the absolute value of the pixel value of the texture image, or may be defined by the difference between the maximum value and the minimum value of the pixel value of the texture image. The calculated amplitude value MA(t) is output to the reference amplitude update determination section 342.

The reference amplitude update determination section 342 receives the amplitude value MA(t) output from the amplitude calculation section 341 and the reference amplitude determination threshold value output from the correction amount control section 345, and determines whether or not to select the amplitude value MA(t) as a new reference amplitude value based on the preceding amplitude values MA(t−1) and MA(t−2) stored in the reference amplitude update determination section 342.

Figure 6:
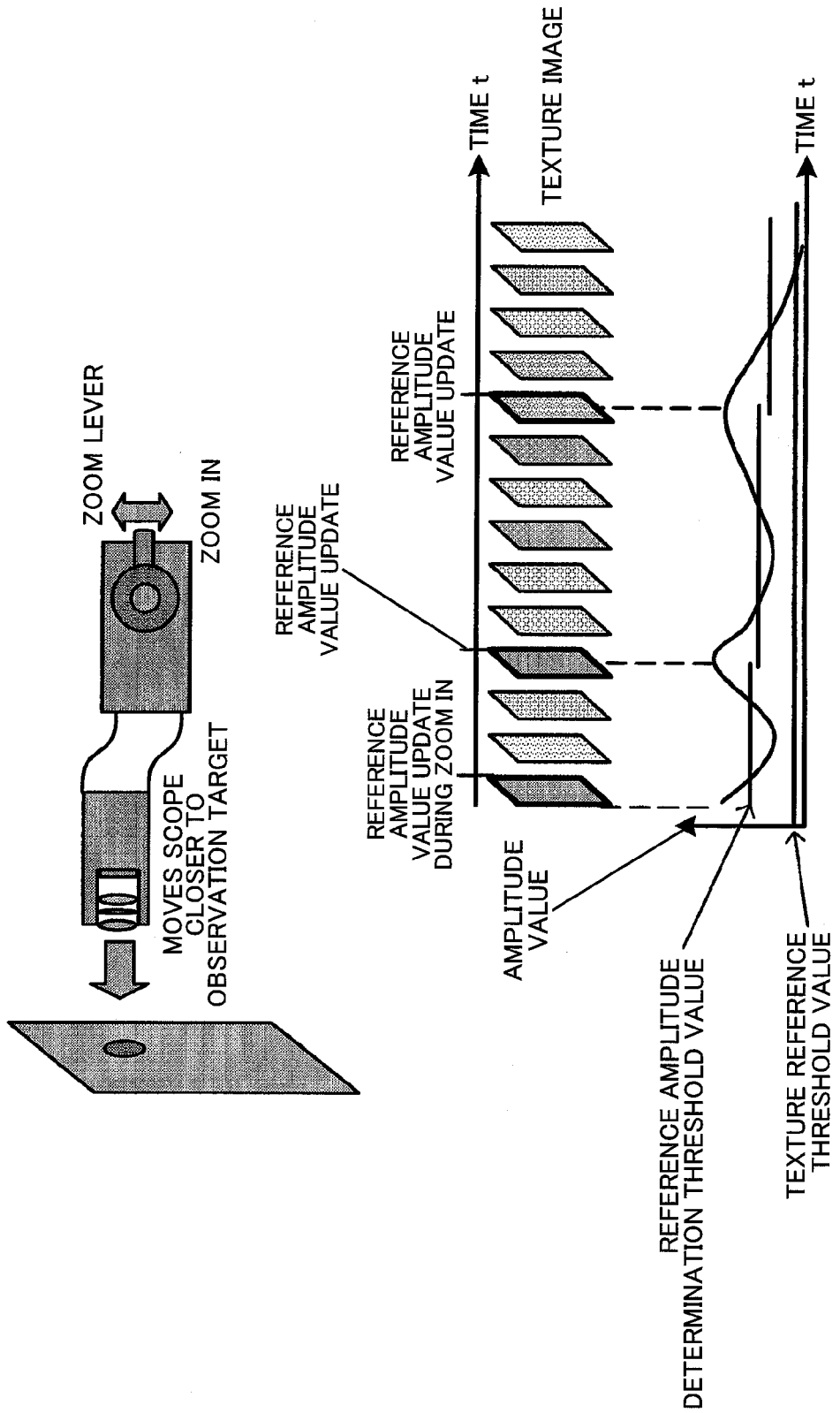
FIG. 6 is a view illustrating an observation state switch operation using a zoom lever and a reference amplitude value update process.

The details of the above process are described below with reference to FIG. 6 (schematic view). The correction amount control section 345 outputs the texture reference threshold value to the reference amplitude update determination section 342 as the reference amplitude determination threshold value immediately after the observation mode has changed to the zoom observation mode. Therefore, the amplitude value of the texture image when the observation mode has changed to the zoom observation mode is selected as the reference amplitude value, and output to the reference amplitude storage section 343 except for the case where blur or defocus has occurred due to a large motion, or the case where defocus has occurred due to too short a distance from the observation target, for example.

Since the average value of the texture reference threshold value and the reference amplitude value is used as the reference amplitude determination threshold value in a state in which the zoom observation mode is maintained, the reference amplitude determination threshold value for updating the reference amplitude value is set to a larger value. This makes it possible to suppress a situation in which the reference amplitude value is frequently updated. The above control process aims at suppressing a temporal change in resolution of the defocus-corrected image that is output from the blending section 370 and changes in synchronization with the reference amplitude value by suppressing a situation in which the reference amplitude value frequently changes. This makes it possible to apparently maintain an in-focus state.

The user operates the endoscope during zoom observation so that the desired magnification and an in-focus state are maintained by operating the zoom lever while moving the end of the scope closer to the observation target. However, since the depth of field decreases as the magnification increases (i.e., an in-focus state cannot be maintained), an in-focus state and a defocused state repeatedly occur (see the time-amplitude value graph illustrated in FIG. 6).

The reference amplitude update determination section 342 determines whether the amplitude value has a maximum value in a period between the time t−2 and the time t from the amplitude values MA(t), MA(t−1), and MA(t−2). For example, the reference amplitude update determination section 342 determines whether a maximum value is present in the above period by performing quadratic fitting on the amplitude values MA(t), MA(t−1), and MA(t−2). When a maximum value is present in the above period, the maximum value calculated by the quadratic expression is determined to be a candidate for the reference amplitude value, and compared with the reference amplitude determination threshold value. When the maximum value is larger than the reference amplitude determination threshold value, the maximum value is output to the reference amplitude storage section 343 as the reference amplitude value. When the maximum value is equal to or smaller than the reference amplitude determination threshold value, the maximum value is not output to the reference amplitude storage section 343 (i.e., the maximum value is not regarded as the reference amplitude value). When a minimum value has been detected, the minimum value is not compared with the reference amplitude determination threshold value (i.e., the reference amplitude value is not changed).

The reference amplitude value is updated as described above in order to deal with a temporal change in characteristics of the texture image (e.g., when the mucous membrane structure or blood vessels (i.e., observation target) that are not resolved at a low magnification are resolved due to the difference in observation magnification, or when the observation position has been changed in a zoom observation state).

The reference amplitude storage section 343 receives the reference amplitude value output from the reference amplitude update determination section 342, and updates the reference amplitude value stored therein with the latest value. The latest reference amplitude value is output to the correction amount control section 345 and the correction amount calculation section 344.

The correction amount calculation section 344 receives the amplitude value MA(t) (i.e., the amplitude value at the time t) output from the amplitude calculation section 341, the reference amplitude value RMA output from the reference amplitude storage section 343, and the correction amount upper limit output from the correction amount control section 345, and calculates the correction amount from the amplitude gain at which the amplitude value MA(t) is equal to the reference amplitude value RMA, and the threshold values Th1 and Th2. The calculated correction amount is output to the texture correction section 360.

Correction amount=amplitude gain−1 (5)

where, amplitude gain≥1 and amplitude gain<Th1.

Correction amount=correction amount upper limit−
α×amplitude gain+β (6)

where, amplitude gain≥Th1 and amplitude gain<Th2.

Correction amount=0 (7)

where, amplitude gain<1 or amplitude gain≥Th2.
Th1=correction amount upper limit+1, Th2=Th1+reference amplitude value/texture reference threshold value
α=amplitude upper limit/(Th2−Th1)
β=α×Th2−correction amount upper limit
Amplitude gain=RMA/MA(t)

Figure 7:
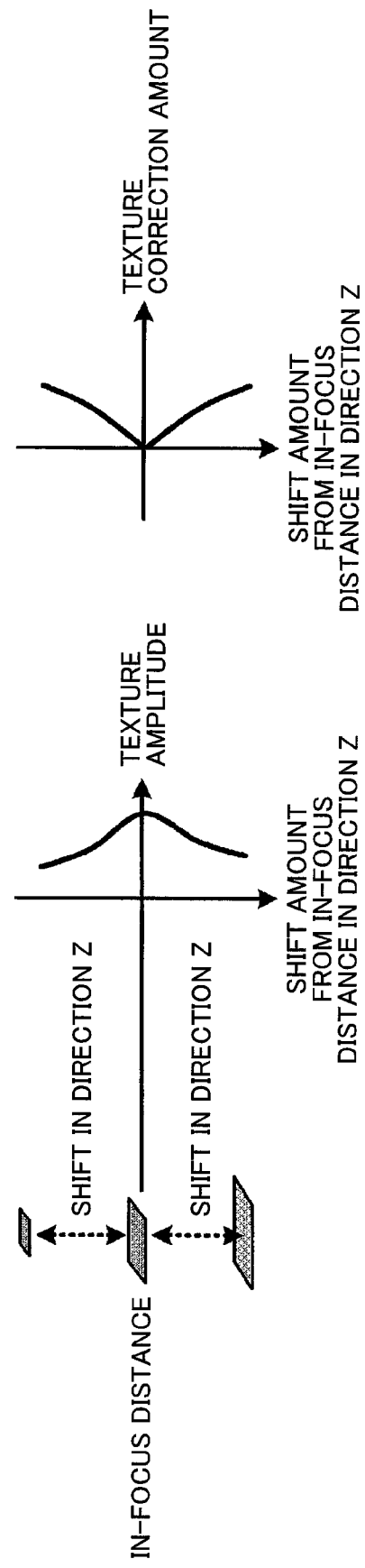
FIGS. 7A to 7C are views illustrating the relationship between shift in a direction Z and a correction amount.

The relationship between the amplitude value of the texture image and the correction amount is described below with reference to FIGS. 7A to 7C (schematic views). When the end of the scope and the observation target are positioned so that the shift amount from the in-focus distance in a direction Z (i.e., the optical axis direction of the optical system provided at the end of the scope) is ±Δ that exceeds the depth-of-field range, the amplitude value of the texture image becomes a maximum at the in-focus distance (see FIGS. 7A and 7B). Specifically, an in-focus image and a defocused image are successively observed during zoom observation when the shift amount is +Δ (i.e., a time-series display image that sufficiently utilizes the resolution of the optical system is not observed).

In order to deal with the above problem, the texture correction section 360 outputs a corrected texture image generated by correcting a decrease in amplitude value of the texture image due to the shift in the direction Z so that the texture image has the amplitude value that corresponds to the in-focus distance. Since the blending section 370 sums the corrected texture image and the time-series display image output from the image composition processing section 310, an image that includes the texture (i.e., the mucous membrane structure, blood vessels, and the like in the surface of tissue) can be provided to the user unless the image is not completely defocused even when the end of the scope is not positioned at the in-focus distance.

Although an example in which the texture extraction process is performed on the final display image has been described above, the texture extraction process need not necessarily be performed on the final display image. For example, the texture extraction process may be incorporated in the enhancement process performed by the image composition processing section 310.

Although an example in which the texture extraction process is performed using two bilateral filters has been described above, another configuration may also be employed. For example, the texture image may be simply extracted using a high-pass filter (i.e., a filter that extracts a component having a frequency equal to or higher than a specific frequency) or a band-pass filter. In this case, a stable control process can be implemented by suppressing the effects of the correction amount on the texture image as much as possible by blocking a bright spot area (e.g., a bright spot area due to specular reflection of illumination light from the object) using a process that removes a steep edge that changes with the lapse of time (e.g., a determination process that compares the brightness level with a threshold value that is set based on the average brightness of the image, and a determination area deletion process (e.g., morphological process)).

According to the first embodiment, since a defocused state due to a shift in the direction Z is corrected at a shallow depth of field during zoom observation, the user can closely examine a lesion area within a short time without stress, and the burden imposed on the patient can be reduced.

The endoscope apparatus according to the first embodiment includes an image acquisition section that acquires a captured image in a zoom observation state in time series, a defocus amount information extraction section that extracts defocus amount information from the captured image in the zoom observation state, and a defocus amount correction section that corrects the captured image based on the extracted defocus amount information.

Figure 2:
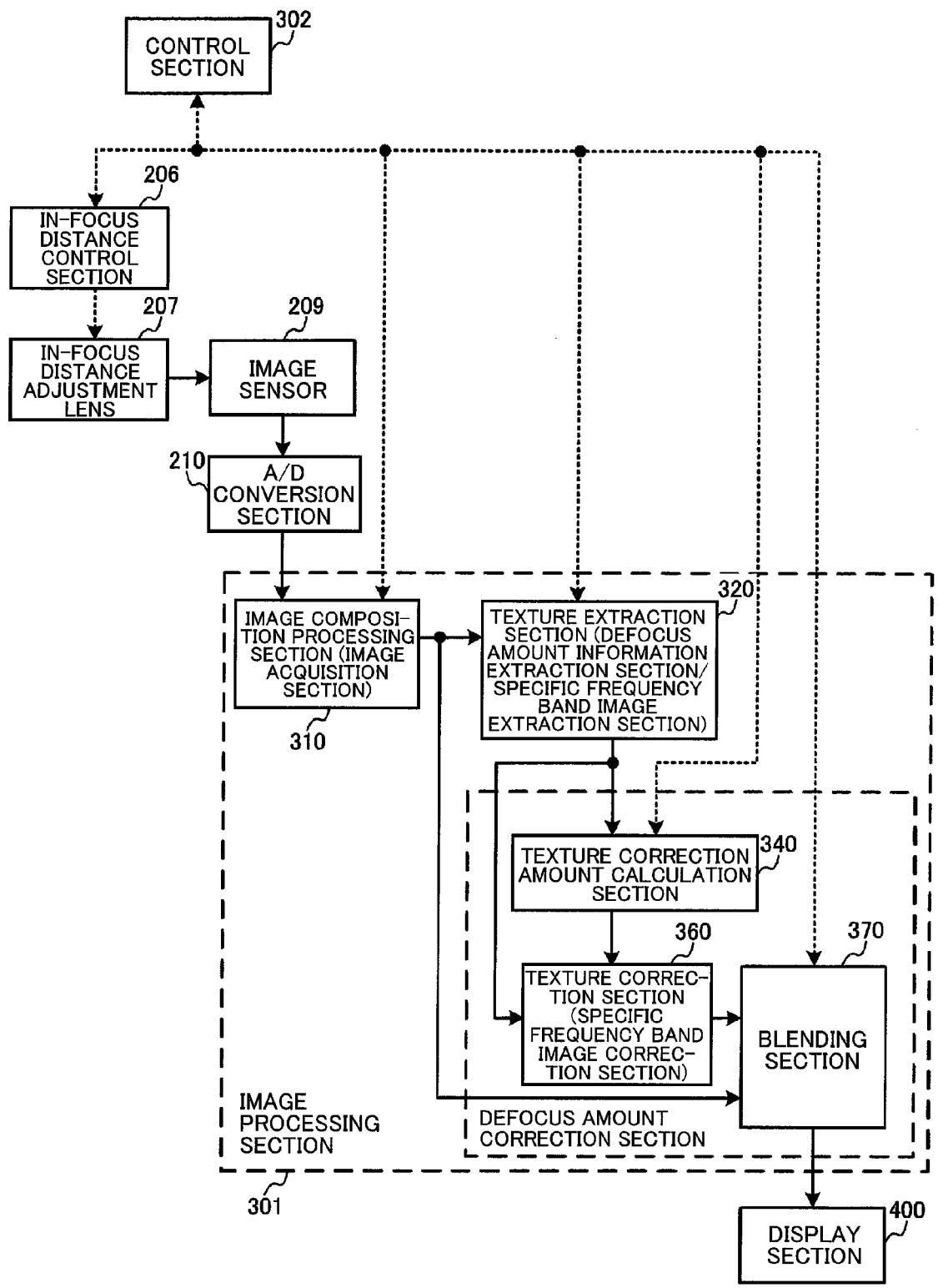
FIG. 2 illustrates a configuration example of an image processing section.

The image acquisition section corresponds to the image composition processing section 310 illustrated in FIG. 2. The defocus amount information extraction section corresponds to the texture extraction section 320 illustrated in FIG. 2. The defocus amount correction section corresponds to the texture correction amount calculation section 340, the texture correction section 360, and the blending section 370 illustrated in FIG. 2.

The term "zoom observation state" used herein refers to an observation state in which the magnification of the optical system is higher than that in a normal observation state. For example, the zoom observation state refers to an observation state in which the magnification of the optical system is several ten to several hundred times. In the first embodiment, the zoom observation state refers to a state in which the magnification of the optical system is equal to or higher than a given magnification.

According to the above configuration, the endoscope apparatus that can implement zoom observation can extract the defocus amount information (i.e., information that indicates the degree of defocus of the captured image) from the captured image during zoom observation, and correct the captured image based on the extracted defocus amount information. As described above, it becomes difficult to acquire an in-focus image as the imaging magnification of the optical system of the endoscope apparatus increases due to a decrease in depth of field. However, it is desirable to acquire an in-focus image since the user (doctor) utilizes the endoscope apparatus for performing diagnosis and procedures. Therefore, it is very useful to perform the defocus restoration process using the method according to the first embodiment. Moreover, since the correction process is performed based on the defocus amount information that indicates the degree of defocus of the captured image, it is possible to prevent a situation in which an excessive correction process (e.g., a correction process that also enhances a noise component) is performed, and acquire a defocus-corrected image that does not produce a wrong visual impression.

The defocus amount information extraction section may include a specific frequency band image extraction section that extracts a specific frequency band image (texture image) from the captured image, the specific frequency band image being an image of a specific frequency band component.

The specific frequency band image extraction section corresponds to the texture extraction section 320 illustrated in FIG. 2.

The above configuration makes it possible to extract an image of the specific frequency band component included in the captured image as the defocus amount information. It is possible to extract an area that is significantly affected by a defocused state (e.g., the surface of the mucous membrane of tissue or a fine structure such as the blood vessel structure) without extracting an area that is affected by a defocused state to only a small extent or an area corresponding to a noise component by appropriately setting the specific frequency when extracting the specific frequency band image. This makes it possible to appropriately extract only the correction target area.

The specific frequency band image extraction section may include a captured image amplitude calculation section that calculates the amplitude value of the captured image.

The amplitude value of the captured image is determined by the difference between the pixel value of the attention pixel (i.e., the amplitude value calculation target pixel) and the pixel value of the peripheral pixel (i.e., a pixel around the attention pixel).

Figure 3:
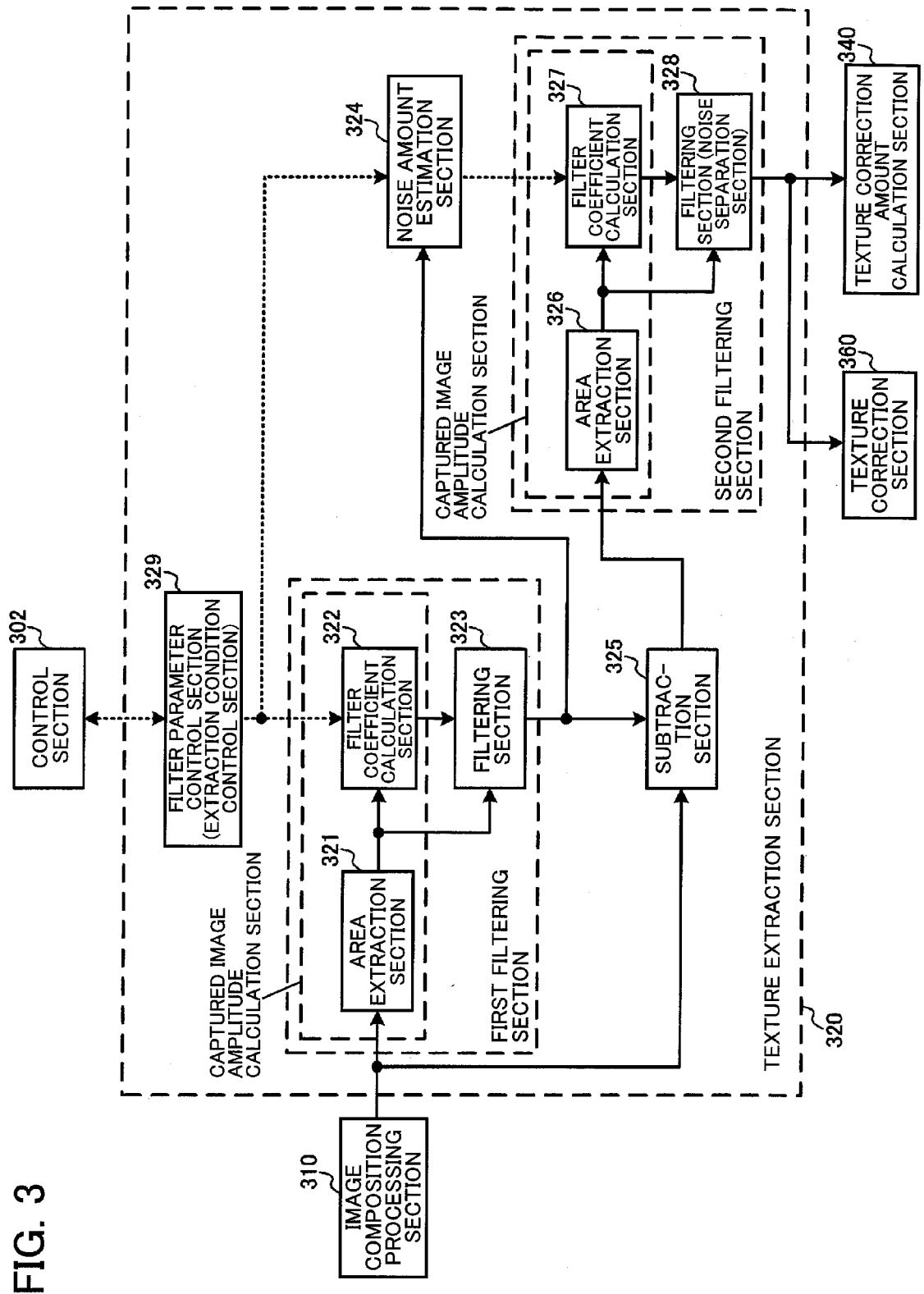
FIG. 3 illustrates a configuration example of a texture extraction section.

The captured image amplitude calculation section corresponds to the area extraction section 321 and the filter coefficient calculation section 322 illustrated in FIG. 3. The captured image amplitude calculation section also corresponds to the area extraction section 326 and the filter coefficient calculation section 327 illustrated in FIG. 3. The area extraction section 321 or the area extraction section 326 calculates the area of the peripheral pixel of the attention pixel. The filter coefficient calculation section 322 or the filter coefficient calculation section 327 calculates the difference between the pixel value of the attention pixel and the pixel value of the peripheral pixel. The difference between the pixel value of the attention pixel and the pixel value of the peripheral pixel corresponds to $|P(x, y, t)-P(x0, y0, t)|$ in the expression (1) or $|D(x, y, t)-D(x0, y0, t)|$ in the expression (3).

This makes it possible to calculate the amplitude value of the captured image. Therefore, a process corresponding to the amplitude value can be implemented to extract an image that excludes a structure (e.g., folds) having a large amplitude value, and corresponds to a structure (e.g., mucous membrane or blood vessel) having a small amplitude value.

The specific frequency band image extraction section may not extract the specific frequency band image when the amplitude value calculated by the captured image amplitude calculation section is within a first amplitude range, and may extract the specific frequency band image when the amplitude value calculated by the captured image amplitude calculation section is within a second amplitude range.

Figure 4:
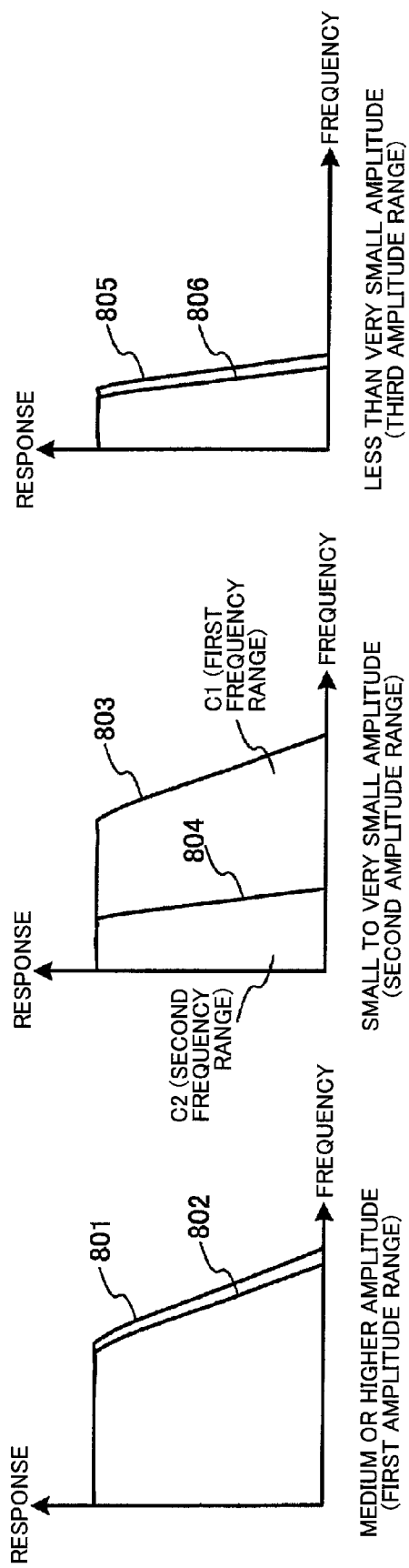
FIGS. 4A to 4C are views illustrating a situation in which a frequency range to be extracted changes corresponding to an amplitude range.

The first amplitude range corresponds to FIG. 4A, and the second amplitude range corresponds to FIG. 4B, for example. Specifically, the amplitude value within the first amplitude range is larger than the amplitude value within the second amplitude range. More specifically, an image within the first amplitude range is an image that corresponds to the folds on the surface of tissue, and an image within the second amplitude range is an image that corresponds to the surface of the mucous membrane and blood vessels.

This makes it possible to implement a process corresponding to the amplitude value of the captured image. More specifically, an image within the first amplitude range (i.e., a range in which the amplitude value is large) is not extracted as the specific frequency band image, and an image within the second amplitude range (i.e., a range in which the amplitude value is smaller than the amplitude value within the first amplitude range) is extracted as the specific frequency band image. This makes it possible to extract only a structure (e.g., mucous membrane or blood vessel) having a small amplitude value without extracting a structure (e.g., folds) having a large amplitude value. Specifically, only an area that is significantly affected by a defocused state can be extracted, and an efficient defocus correction process can be implemented.

The specific frequency band image extraction section may not extract the specific frequency band image when the amplitude value calculated by the captured image amplitude calculation section is within a third amplitude range.

The third amplitude range corresponds to FIG. 4C, for example. Specifically, the amplitude value within the third amplitude range is smaller than the amplitude value within the second amplitude range. More specifically, an image within the third amplitude range is an image that corresponds to noise.

This makes it possible to implement a process corresponding to the amplitude value of the captured image. More specifically, an image within the third amplitude range (i.e., a range in which the amplitude value is smaller than the amplitude value within the second amplitude range) is not extracted as the specific frequency band image. This makes it possible to not extract an image that corresponds to a noise component having an amplitude value smaller than that of the mucous membrane, blood vessels, and the like. Specifically, the defocus restoration process can be performed while preventing a situation in which the noise component is also enhanced.

The specific frequency band image may be an image that has an amplitude value within the second amplitude range and a frequency component within a first frequency range.

The first frequency range corresponds to the range indicated by C1 in FIG. 4B, and a second frequency range corresponds to the range indicated by C2 in FIG. 4B. Specifically, the frequency within the first frequency range is higher than the frequency within the second frequency range.

This makes it possible to extract only the specific frequency range in addition to the specific amplitude range to obtain the specific frequency band image. An efficient defocus correction process can be implemented by adjusting the extraction target first frequency range to the intensive observation target area (i.e., an area for which it is desired to appropriately perform the defocus correction process).

The specific frequency band image extraction section may include an extraction condition control section that controls an extraction condition for the specific frequency band image based on magnification information about the optical system of the endoscope apparatus.

The extraction condition control section corresponds to the filter parameter control section 329 illustrated in FIG. 3.

This makes it possible to control the extraction condition for the specific frequency band image based on the magnification information about the optical system. Therefore, the specific frequency band image can be appropriately extracted even when the observation target tissue structure has changed corresponding to the magnification.

When the frequency within the first frequency range is higher than the frequency within the second frequency range (see C1 and C2 in FIG. 4B), the first frequency range may be a frequency range that is larger than a first frequency threshold value and is smaller than a second frequency threshold value. For example, the first frequency threshold value corresponds to the cut-off frequency of the filter 804 illustrated in FIG. 4B, and the second frequency threshold value corresponds to the cut-off frequency of the filter 803 illustrated in FIG. 4B, for example. Note that the frequency threshold value is not limited to the cut-off frequency of a filter. The specific frequency band image may have a frequency component within the first frequency range. In this case, the specific frequency band image extraction section may increase the first frequency threshold value and the second frequency threshold value as a magnification indicated by the magnification information about the optical system of the endoscope apparatus increases.

This makes it possible to implement the process illustrated in FIGS. 19A to 19C. As illustrated in FIGS. 19A to 19C, the first frequency range (i.e., the extraction target frequency range) may be shifted in the direction in which the frequency increases as the magnification of the optical system increases. This makes it possible to appropriately extract the frequency range that corresponds to an important observation target corresponding to the magnification. More specifically, a large reddened or faded area that shows a subtle change in color is important when the magnification is low, the structure of the gland duct and the blood vessel distribution pattern are important when the magnification is medium, and the structure of the fine pit pattern and the fine blood vessels in the mucosal surface layer are important when the magnification is high.

The specific frequency band image extraction section may include a first filtering section, the subtraction section 325, the noise amount estimation section 324, and a second filtering section (see FIG. 3). The first filtering section may perform a first filter process, and the subtraction section 325 calculates the difference between the image obtained by the first filter process and the captured image to generate a structural image. The noise amount estimation section may estimate the noise amount of the structural image based on the extraction condition, and the second filtering section may separate noise from the structural image to acquire the specific frequency band image.

The term "structural image" used herein refers to an image that is generated when extracting the specific frequency band image (texture image) from the captured image. More specifically, an image that is output from the image composition processing section 310 and input to the first filtering section (area extraction section 321) and the subtraction section 325 is the captured image, and an image obtained by the subtraction section 325 as a result of calculating the difference between the output from the first filtering section and the captured image is the structural image. The structural image is input to the second filtering section (area extraction section 326), and subjected to the second filter process, and the specific frequency band image (texture image) is output from the second filtering section (filtering section 328).

The above configuration makes it possible to extract the specific frequency band image by the two-stage filter process. More specifically, the first filter process is performed using the first-stage filter (described in detail later), and noise is removed using the second-stage filter.

The defocus amount information extraction section may include a captured image amplitude calculation section that calculates the amplitude value of the captured image. The first filtering section may subject an image of which the amplitude value calculated by the captured image amplitude calculation section is within the first amplitude range to a low-pass filter process that allows a frequency component that corresponds to the first frequency range and the second frequency range to pass through. The first filtering section may subject an image of which the amplitude value calculated by the captured image amplitude calculation section is within the second amplitude range to a low-pass filter process that allows a frequency component that corresponds to the second frequency range to pass through, and blocks a frequency component that corresponds to the first frequency range.

This makes it possible to implement a process corresponding to the reference sign 802 in FIG. 4A and the reference sign 804 in FIG. 4B. Specifically, a process that allows a high-frequency component to remain is performed on an image having a large amplitude value (corresponding to folds or the like), and a process that blocks a high-frequency component is performed on an image having a small amplitude value (corresponding to the surface of the mucous membrane, blood vessel, or the like). Since the subtraction section calculates the difference between the captured image and the image obtained by the filter process, the image having a large amplitude value contains only the frequency component higher than the first frequency range, while the image having a small amplitude value also contains the frequency component within the first frequency range.

The first filtering section may include the extraction target area extraction section 321 that extracts a given area around the attention pixel from the captured image (see FIG. 3). The first filtering section may include the filter coefficient calculation section 322 that calculates the spatial distance and the difference in pixel value between the attention pixel and the peripheral pixel, and calculates the filter coefficient based on the extraction condition. The first filtering section may also include the filtering section 323 that performs the filter process based on the given area extracted by the area extraction section 321 and the filter coefficient calculated by the filter coefficient calculation section 322.

This makes it possible to implement the filter process using the structure illustrated in FIG. 3. More specifically, the peripheral area of the attention pixel is extracted, and the peripheral pixel is set. The spatial distance and the difference in pixel value between the attention pixel and the peripheral pixel are calculated, and the filter coefficient is calculated based on the extraction condition. Specifically, $\{(x-x0)^2+(y-y0)^2\}$ and $|P(x, y, t)-P(x0, y0, t)|$ in the expression (1) are calculated. The filter process is performed using the expression (2) based on the filter coefficient calculated using the expression (1). Therefore, the amplitude value $|P(x, y, t)-P(x0, y0, t)|$ is largely involved in the filter coefficient, and the extraction process corresponding to the amplitude range can be implemented. Since the index value $\sigma 1s$ is also adjusted, the amplitude range can be appropriately set corresponding to the condition.

The defocus amount information extraction section may include a captured image amplitude calculation section that calculates the amplitude value of the captured image. The second filtering section may subject an image of which the amplitude value calculated by the captured image amplitude calculation section is within the second amplitude range to a low-pass filter process that allows a frequency component that corresponds to the first frequency range and the second frequency range to pass through. The second filtering section may subject an image of which the amplitude value calculated by the captured image amplitude calculation section is within the third amplitude range to a low-pass filter process that allows a frequency component that corresponds to the second frequency range to pass through, and blocks a frequency component that corresponds to the first frequency range.

This makes it possible to implement a process corresponding to the reference sign 803 in FIG. 4B and the reference sign 805 in FIG. 4C. Specifically, a process that allows a high-frequency component to remain is performed on an image having a small amplitude value (corresponding to the surface of the mucous membrane, blood vessel, or the like), and a process that blocks a high-frequency component is performed on an image having a smaller amplitude value (corresponding to noise). Since the above filter process is performed after the first filter process, a frequency component that corresponds to the first frequency range remains in the image within the second amplitude range, but is almost completely removed from the image within the third amplitude range. This makes it possible to remove noise.

The second filtering section may include the area extraction section 326 that extracts a given area around the attention pixel from the captured image (see FIG. 3). The second filtering section may include the filter coefficient calculation section 327 that calculates the spatial distance and the difference in pixel value between the attention pixel and the peripheral pixel, and calculates the filter coefficient based on the extraction condition. The second filtering section may also include a noise separation section (corresponding to the filtering section 328 illustrated in FIG. 3) that performs a filter process based on the given area extracted by the area extraction section 326 and the filter coefficient calculated by the filter coefficient calculation section 327 to separate noise.

This makes it possible to implement the filter process using the structure illustrated in FIG. 3. More specifically, the peripheral area of the attention pixel is extracted, and the peripheral pixel is set. The spatial distance and the difference in pixel value between the attention pixel and the peripheral pixel are calculated, and the filter coefficient is calculated based on the extraction condition. Specifically, $\{(x-x0)^2+(y-y0)^2\}$ and $|D(x, y, t)-D(x0, y0, t)|$ in the expression (3) are calculated. The filter process is performed using the expression (4) based on the filter coefficient calculated using the expression (3). Therefore, the amplitude value $|D(x, y, t)-D(x0, y0, t)|$ is largely involved in the filter coefficient, and the extraction process corresponding to the amplitude range can be implemented. Since the index value $\sigma 2s$ is also adjusted, the amplitude range can be appropriately set corresponding to the condition.

The defocus amount correction section may correct the captured image acquired in time series based on the defocus amount of an in-focus captured image that is a captured image that has been determined to be in focus.

The defocus amount correction section corresponds to the texture correction amount calculation section 340, the texture correction section 360, and the blending section 370 illustrated in FIG. 2.

This makes it possible to set a correction reference. Since the in-focus captured image is an image that has been determined to be in focus, an image that is defocused to only a small extent can be acquired by performing the correction process (e.g., amplification of the signal value) up to the level of the in-focus captured image.

The defocus amount correction section may include a specific frequency band image amplitude calculation section that calculates the amplitude value of the specific frequency band image extracted by the specific frequency band image extraction section.

Figure 5:
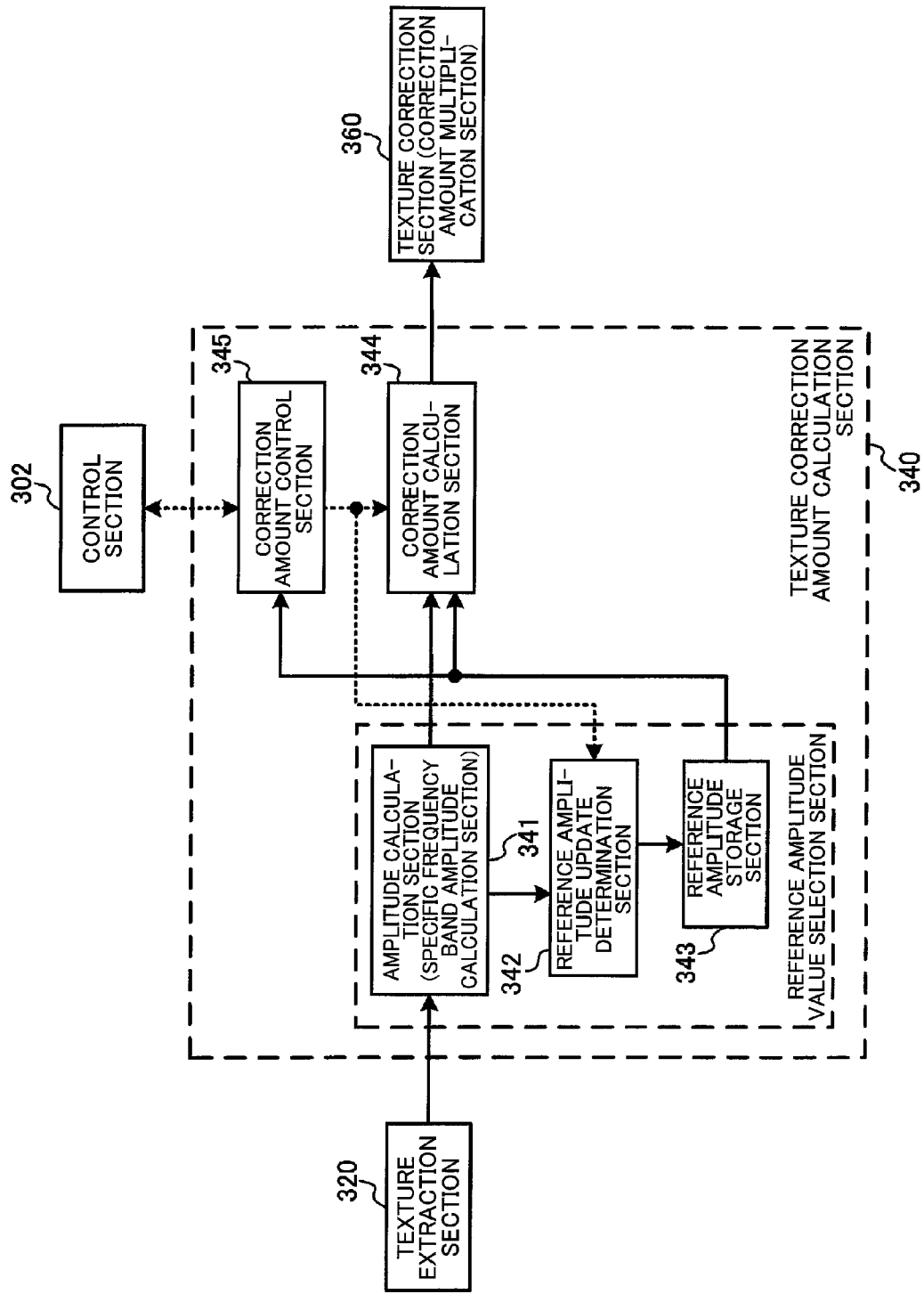
FIG. 5 illustrates a configuration example of a texture correction amount calculation section.

The specific frequency band image amplitude calculation section corresponds to the amplitude calculation section 341 illustrated in FIG. 5. The amplitude value of the specific frequency band image may be defined by the maximum value of the absolute value of the pixel value of the specific frequency band image, or may be defined by the difference between the maximum value and the minimum value of the pixel value of the specific frequency band image.

This makes it possible to calculate the amplitude value of the specific frequency band image. Therefore, the amplitude value of the image can be used as the correction reference. Specifically, a defocused image can be corrected by amplifying the amplitude value of the defocused image to be equal to the amplitude value of the in-focus image.

The defocus amount correction section may include a specific frequency band image correction section (corresponding to the texture correction section 360) that corrects the specific frequency band image based on the amplitude value of the specific frequency band image calculated by the specific frequency band image amplitude calculation section, and the blending section 370 that blends the captured image and the corrected specific frequency band image.

This makes it possible to implement the correction process by correcting the specific frequency band image, and blending the corrected specific frequency band image and the captured image. Since the specific frequency band image is an image that is significantly affected by a defocused state and corresponds to an important observation target, it is possible to implement a correction process that maintains the observation target at a resolution almost equal to that achieved in an in-focus state by extracting only the correction target image, correcting the extracted image, and blending the corrected image and the captured image.

The specific frequency band image correction section may include a reference amplitude value selection section (corresponding to the reference amplitude update determination section 342 illustrated in FIG. 5) that selects an amplitude value that has been determined to be in focus from the amplitude value calculated in time series by the specific frequency band image amplitude calculation section as a reference amplitude value, and a correction amount multiplication section (corresponding to the correction amount calculation section 344 and the texture correction section 360 illustrated in FIG. 5) that calculates and multiplies the correction amount for the specific frequency band image based on the reference amplitude value.

This makes it possible to calculate the reference amplitude value, and perform the correction process based on the calculated reference amplitude value. For example, the correction process is performed so that the amplitude value of the defocused image is equal to the reference amplitude value (1<amplitude gain<Th1 in FIG. 18). In FIG. 18, the degree of correction is reduced when the amplitude gain is larger than a given value (i.e., when the amplitude value of the defocused image is smaller than the reference amplitude value) since the correction process does not properly function due to too high a degree of defocus.

The in-focus captured image may be a captured image acquired when the optical system has been switched to the zoom observation state.

This makes it possible to efficiently acquire the in-focus captured image. Specifically, since it is likely that the captured image is in focus when the optical system has been switched to the zoom observation state, a significant problem does not occur even if the captured image acquired when the optical system has been switched to the zoom observation state is used as the in-focus captured image. Therefore, the in-focus captured image can be acquired by a simple process without performing a determination process based on a condition (described below).

The in-focus captured image may be a captured image that has been acquired after the optical system has been switched to the zoom observation state, and has an amplitude value that has satisfied a given condition within a given period. For example, the given condition may be a condition whereby the amplitude value is larger than the reference amplitude determination threshold value and has a maximum value.

This makes it possible to update the in-focus captured image (i.e., reference image) (i.e., update the reference amplitude value) after the optical system has been switched to the zoom observation state. The observation magnification may change, or the observation target object may change due to large lateral movement or the like during observation using an endoscope, whereby the amplitude value of the image may change. In such a case, an appropriate reference can be set by updating the in-focus captured image. It is also possible to prevent a situation in which the update process is frequently performed by setting an update condition for the in-focus captured image.

The first embodiment also relates to a program that causes a computer to function as an image acquisition section that acquires a captured image in a zoom observation state in time series, a defocus amount information extraction section that extracts defocus amount information from the captured image in the zoom observation state, and a defocus amount correction section that corrects the captured image based on the extracted defocus amount information.

This makes it possible to apply the first embodiment to a system (e.g., imaging apparatus and endoscope apparatus) that acquires an image, and processes the image, and a system that stores image data, and processes the stored image data by software processing using a computer system (e.g., PC), for example. The program is stored in an information storage device. The information storage device may be an arbitrary recording medium that is readable by an optical detection system, such as an optical disk (e.g., DVD and CD), a magnetooptical disk, a hard disk (HDD), and a memory (e.g., nonvolatile memory and RAM).

3. Second Embodiment 3.1 Configuration

Figure 10:
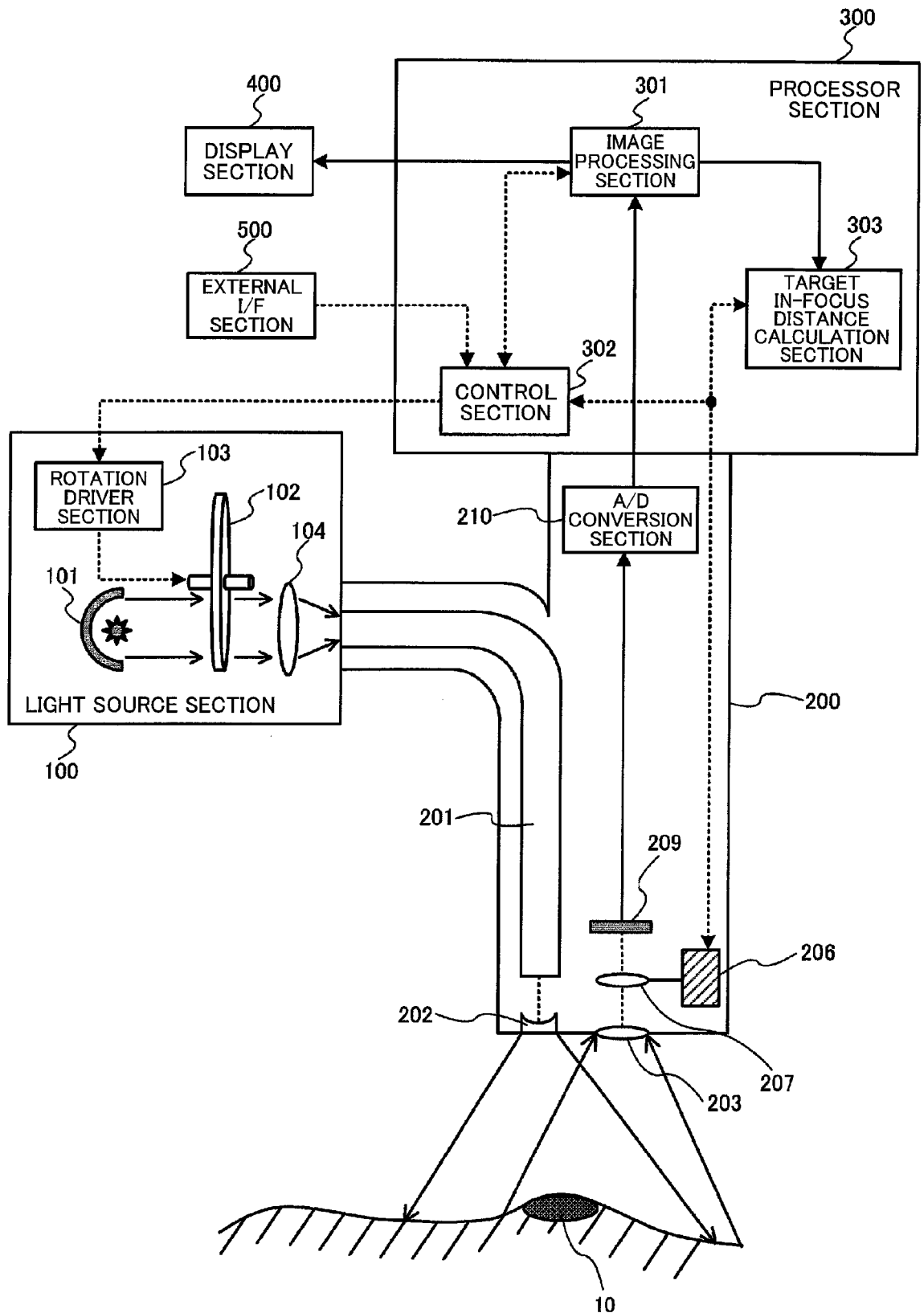
FIG. 10 illustrates another system configuration example of an endoscope apparatus according to one embodiment of the invention.

FIG. 10 is a block diagram illustrating the overall configuration of an imaging system according to the second embodiment. The imaging system according to the second embodiment includes a light source section 100, an imaging section 200, a processor section 300, a display section 400, and an external I/F section 500, and is basically configured in the same manner as described above in connection with the first embodiment. The differences from the first embodiment are mainly described in detail below.

The light source section 100 includes a white light source 101, a rotary color filter 102 that has a plurality of spectral transmittances, a rotation driver section 103 that drives the rotary color filter 102, and a condenser lens 104 that focuses light that has passed through the rotary color filter 102 and has spectral characteristics on the incident end face of a light guide fiber 201.

Figure 8:
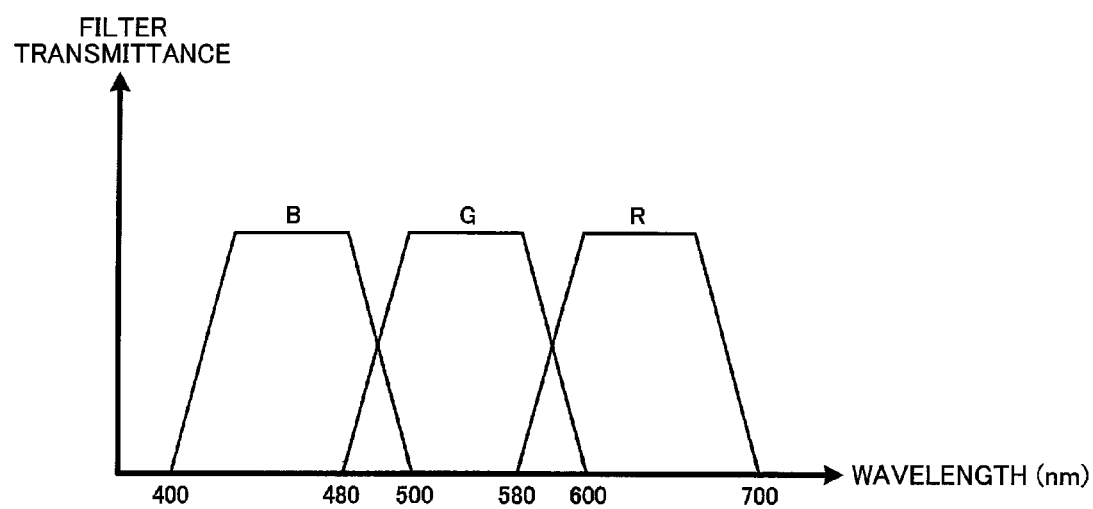
FIG. 8 illustrates the transmittance of a color filter.
Figure 9:
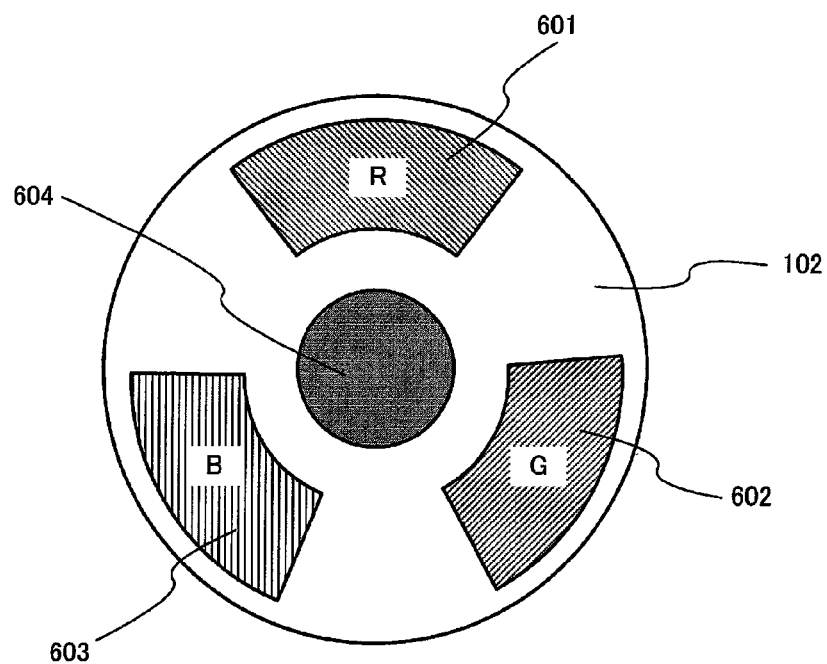
FIG. 9 illustrates a configuration example of a rotary filter.

As illustrated in FIG. 9, the rotary color filter 102 includes a red color filter 601, a green color filter 602, a blue color filter 603, and a rotary motor 604, for example. The red color filter 601, the green color filter 602, and the blue color filter 603 have the spectral characteristics illustrated in FIG. 8.

The rotation driver section 103 rotates the rotary color filter 102 at a given rotational speed in synchronization with the imaging period of an image sensor 209 based on a control signal output from a control section 302 included in the processor section 300. For example, when the color filter is rotated at 20 revolutions per second, each color filter crosses the incident white light every 1/60th of a second, and the image sensor 209 captures and transfers a reflected light image of each color light (R, G, or B) every 1/60th of a second. The image sensor 209 is a monochrome image sensor. Specifically, an endoscope apparatus according to the second embodiment frame-sequentially captures an R image, a G image, and a B image every 1/60th of a second, and the frame rate is 20 fps.

A monochrome single-chip image sensor is used as the image sensor 209 of the imaging section 200. An in-focus distance control section 206 and an in-focus distance adjustment lens 207 can be driven at a high speed so that an autofocus process can be implemented in real time.

The processor section 300 additionally includes a target in-focus distance calculation section 303. The control process performed by the control section 302 is changed from the control process described above in connection with the first embodiment along with the addition of the target in-focus distance calculation section 303, the rotary color filter 102, and the rotation driver section 103.

The target in-focus distance calculation section 303 included in the processor section 300 receives a time-series display image output from an image processing section 301 and information about the currently applied color filter output from the control section 302, calculates the target in-focus distance based on an image obtained using the corresponding color filter, and outputs the calculated target in-focus distance and the wobbling amount in the direction Z (i.e., the optical axis direction of the end of the scope) to the control section 302.

The control section 302 outputs the moving position of the in-focus distance adjustment lens 207 to the in-focus distance control section 206 based on the target in-focus distance output from the target in-focus distance calculation section 303 to move the in-focus distance adjustment lens 207 before the subsequent color filter crosses the white light source 101.

A texture extraction section 320 extracts a texture image from the time-series display image output from an image composition processing section 310, and outputs the extracted texture image to the target in-focus distance calculation section 303.

A texture correction amount calculation section 340 calculates the correction amount for the texture image based on the texture image extracted by the texture extraction section 320. A texture correction section 360 corrects the texture image based on the calculated correction amount, and a blending section 370 blends the corrected texture image and the captured image output from the image composition processing section to generate a defocus-corrected image.

3.2 Detailed Configuration of Defocus Amount Information Extraction Section

Figure 13:
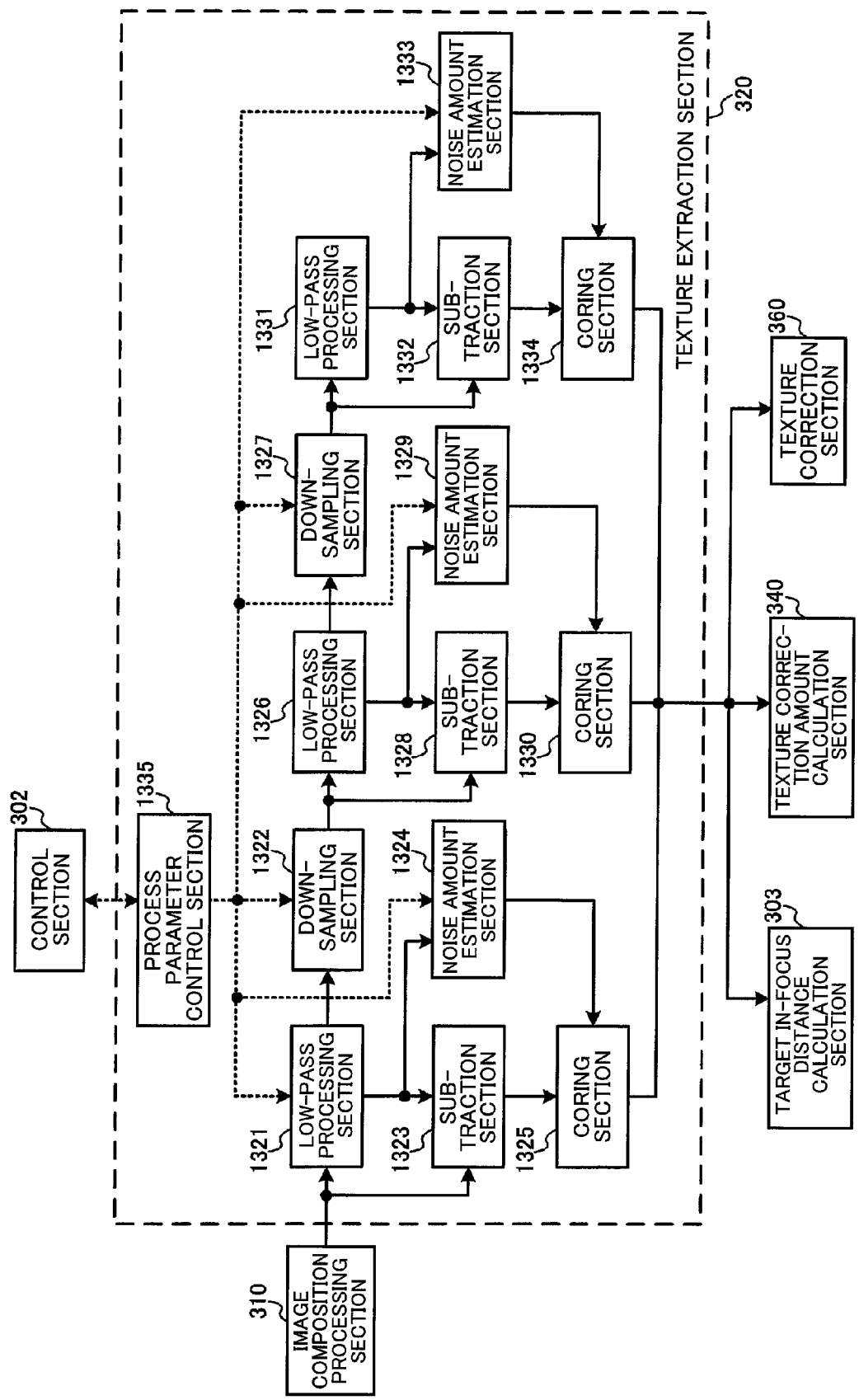
FIG. 13 illustrates another configuration example of a texture extraction section.

The texture extraction section 320 has the configuration illustrated in FIG. 13 (block diagram), differing from the first embodiment.

The texture extraction section 320 includes low-pass processing sections 1321, 1326, and 1331, downsampling sections 1322 and 1327, subtraction sections 1323, 1328, and 1332, noise amount estimation sections 1324, 1329, and 1333, coring sections 1325, 1330, and 1334, and a process parameter control section 1335.

The texture extraction section 320 is configured to divide the time-series display image into a plurality of frequency bands to generate sub-band images, and perform an independent noise reduction process on each sub-band image. The texture extraction process performed while dividing the time-series display image into a plurality of frequency bands is characterized in that the frequency bands into which the time-series display image is divided, are changed corresponding to the frequency band of the observation target texture (mucous membrane structure or blood vessel distribution pattern) according to the zoom observation magnification.

The flow of data transferred between the above sections is described below. The process parameter control section 1335 stores a table that defines the relationship between the magnification information and the bandwidth so that the bandwidth of each frequency band (sub-band) differs corresponding to the magnification information output from the control section 302. FIGS. 14A and 14B illustrate frequency band division examples. FIG. 14A illustrates a frequency band division example when the zoom observation magnification is low, and FIG. 14B illustrates a frequency band division example when the zoom observation magnification is high. In FIGS. 14A and 14B, four frequency bands (1) to (4) are provided.

The magnification information output from the control section 302 is compared with a given threshold value, and the band information division method is determined based on the comparison result. The low-pass filter coefficient corresponding to each frequency band and the reduction ratio during downsampling are then determined. The filter coefficient is output to the low-pass processing sections 1321, 1326, and 1331, and the reduction ratio is output to the downsampling sections 1322 and 1327. The noise amount estimation model corresponding to each frequency band is also changed based on the division method. The noise estimation model corresponding to each frequency band is output to the noise amount estimation sections 1324, 1239, and 1333.

The plurality of frequency bands are then subjected to an identical process. The following description focuses on the process performed on the sub-band image in the frequency band (1). The low-pass processing section 1321 receives the time-series display image output from the image composition processing section 310 and the filter coefficient output from the process parameter control section 1329. The low-pass processing section 1321 performs a filter process on the time-series display image to generate a low-pass time-series display image, and outputs the low-pass time-series display image to the subtraction section 1323, the downsampling section 1322, and the noise amount estimation section 1324.

The subtraction section 1323 receives the time-series display image output from the image composition processing section 310 and the low-pass time-series display image output from the low-pass processing section 1321. The subtraction section 1323 subtracts the low-pass time-series display image from the time-series display image to generate a high-pass time-series display image, and outputs the high-pass time-series display image to the coring section 1325.

The noise amount estimation section 1324 receives the low-pass time-series display image output from the low-pass processing section 1321 and the noise estimation model output from the process parameter control section 1335, converts the pixel value of the low-pass time-series display image into a noise amount using the noise estimation model, and outputs the noise amount to the coring section 1325.

The coring section 1325 receives the high-pass time-series display image output from the subtraction section 1323 and the noise amount output from the noise amount estimation section 1324, and performs a coring process using a coring width corresponding to the noise amount. The high-pass time-series display image subjected to the coring process is output to the texture correction amount calculation section 340, the target in-focus distance calculation section 303, and the texture correction section 360.

The frequency band (1) illustrated in FIG. 14A or 14B is thus extracted. The frequency bands (2) and (3) are extracted in the same manner as described above.

Therefore, description thereof is omitted.

3.3 Detailed Configuration of Defocus Amount Correction Section

Figure 15:
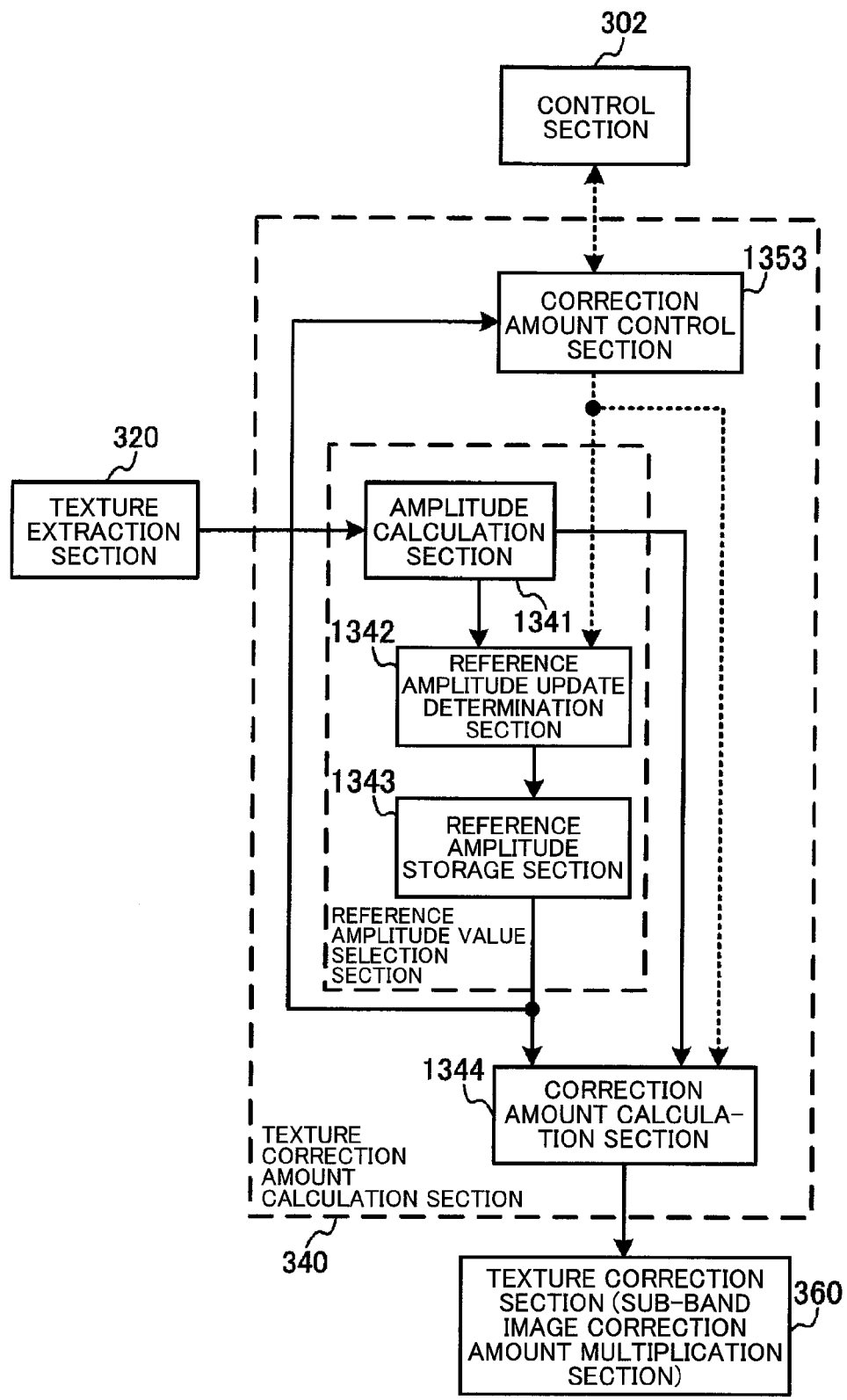
FIG. 15 illustrates another configuration example of a texture correction amount calculation section.

The texture correction amount calculation section 340 is described in detail below with reference to FIG. 15.

The texture correction amount calculation section 340 includes an amplitude calculation section 1341, a reference amplitude update determination section 1342, a reference amplitude storage section 1343, a correction amount calculation section 1344, and a correction amount control section 1353. The texture correction amount calculation section 340 receives the frequency bands (1), (2), and (3) illustrated in FIG. 14A or 14B, and calculates the correction amount for each frequency band.

The following description focuses on calculation of the correction amount for the frequency band (1) illustrated in FIG. 14A or 14B. The correction amount control section 1353 receives the observation mode signal, the texture reference threshold value, and the correction amount upper limit output from the control section 302, and the current reference amplitude value output from the reference amplitude storage section 1343. The correction amount control section 1353 sets a reference amplitude determination threshold value based on the observation mode signal, the texture reference threshold value, and the reference amplitude value, outputs the reference amplitude determination threshold value to the reference amplitude update determination section 1342, and outputs the correction amount upper limit to the correction amount calculation section 1344.

The texture reference threshold value is a reference value for determining whether or not the captured time-series display image is defocused, and varies depending on the imaging performance. Therefore, a different texture reference threshold value is set corresponding to the type of scope. The reference amplitude value determination threshold value is a threshold value for selecting the reference amplitude value (correction target) for the texture image. The reference amplitude value determination threshold value is set to the texture reference threshold value when the observation mode signal has changed to the zoom observation mode, otherwise it is set to the average value of the texture reference threshold value and the reference amplitude value, for example.

The amplitude calculation section 1341 calculates the amplitude value MA(t) of the texture image extracted at the time t and output from the texture extraction section 320. The amplitude value may be defined by the maximum value of the absolute value of the pixel value of the texture image, or may be defined by the difference between the maximum value and the minimum value of the pixel value of the texture image. The calculated amplitude value MA(t) is output to the reference amplitude update determination section 1342.

The reference amplitude update determination section 1342 receives the amplitude value MA(t) output from the amplitude calculation section 1341 and the reference amplitude determination threshold value output from the correction amount control section 1353, and determines whether or not to select the amplitude value MA(t) as the reference amplitude value based on the preceding amplitude values MA(t−1), MA(t−2), MA(t−3), MA(t−4), MA(t−5), MA(t−

6), MA(t−7), and MA(t−8) (8-field period) stored in the reference amplitude update determination section 1342. Note that the term "1-field period" used herein refers to a period (1/60th of a second) in which an R image, a B image, and a G image captured using the R, G, and B color filters are acquired.

Figure 11:
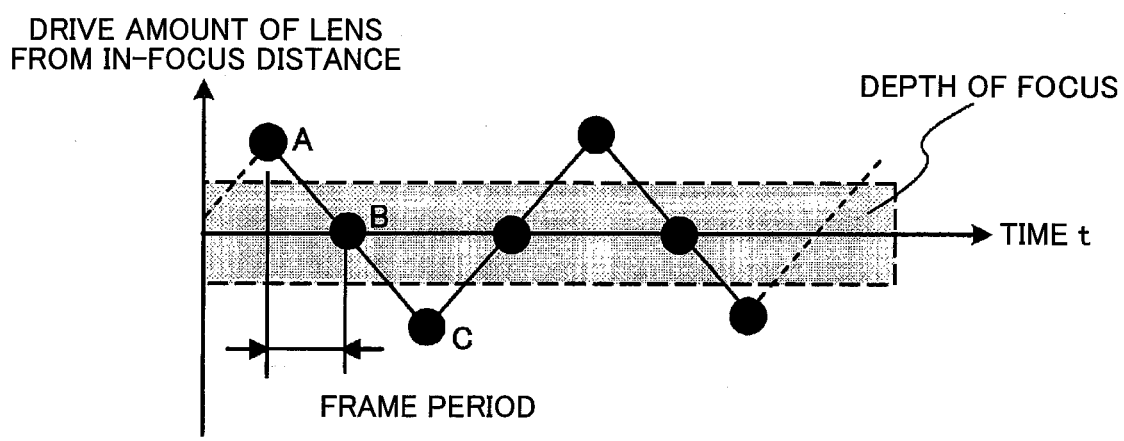
FIG. 11 is a schematic view illustrating an autofocus process that utilizes a contrast method.

The details of the reference amplitude update determination process are described below with reference to FIG. 11 (schematic view). The user operates the endoscope during zoom observation so that the desired magnification is obtained by operating the zoom lever while moving the end of the scope closer to the observation target. In the second embodiment, the user need not take account of an in-focus state since an auto-focus function is provided. However, since the autofocus process is controlled based on the contrast value, it is necessary to estimate the target in-focus distance by capturing an image while wobbling the lens (A→B→C in FIG. 11 (schematic view)) in the direction Z (optical axis direction of the optical system) with respect to the in-focus distance so that a change in contrast occurs. The wobbling process in the direction Z produces an in-focus state and a defocused state.

In particular, a period in which a defocused image is displayed increases (i.e., a change in focus state becomes conspicuous) when the frame rate is low. The frame-sequential endoscope apparatus according to the second embodiment has a low frame rate of 20 fps.

When utilizing a change in contrast for the frame-sequential endoscope apparatus according to the second embodiment, an image is captured at each in-focus distance (A→B→C in FIG. 11) using the R, G, and B filters. Specifically, a transition period from A to B corresponds to one frame period (1/20th of a second).

Since the time-series display image output from the image composition processing section 310 is updated so that only an image captured using the R, G, or B filter (R image, B image, or G image) is updated in the field period, nine texture images are required in order to reliably extract three different texture images corresponding to the R image, the G image, or the B image from a plurality of texture images.

Therefore, the reference amplitude update determination section 1342 determines whether or not nine amplitude values MA(t), MA(t−1), MA(t−2), MA(t−3), MA(t−4), MA(t−5), MA(t−6), MA(t−7), and MA(t−8) corresponding to nine texture images at consecutive times t−8 to t have a maximum value. The reference amplitude update determination section 1342 divides the nine amplitude values into groups {MA(t), MA(t−3), MA(t−6)}, {MA(t−1), MA(t−4), MA(t−7)}, and {MA(t−2), MA(t−5), MA(t−8)}. The reference amplitude update determination section 1342 performs a quadratic fitting process on the three amplitude values of each group to determine whether or not at least one amplitude value has a maximum value.

When a maximum value has been detected, the maximum value calculated using the quadratic expression is used as a candidate for the reference amplitude value. When a plurality of maximum values have been detected, the largest maximum value is selected, and used as a candidate for the reference amplitude value. The candidate for the reference amplitude value is compared with the reference amplitude determination threshold value. When the maximum value is larger than the reference amplitude determination threshold value, the maximum value is output to the reference amplitude storage section 1343 as the reference amplitude value. When the maximum value is equal to or smaller than the reference amplitude determination threshold value, the maximum value is not output to the reference amplitude storage section 1343 (i.e., the maximum value is not regarded as the reference amplitude value). When only a minimum value has been detected from each group, the comparison process using the reference amplitude determination threshold value is not performed, and the reference amplitude value is not changed.

The reference amplitude value is updated for the reasons described above in connection with the first embodiment.

The reference amplitude storage section 1343 receives the reference amplitude value output from the reference amplitude update determination section 1342, and updates the reference amplitude value stored therein with the latest value. The latest reference amplitude value is output to the correction amount control section 1355 and the correction amount calculation section 1344.

The correction amount calculation section 1344 receives the amplitude value MA(t) (i.e., the amplitude value at the time t) output from the amplitude calculation section 1341, the reference amplitude value RMA output from the reference amplitude storage section 1343, and the correction amount upper limit output from the correction amount control section 1353, calculates the amplitude gain at which the amplitude value MA(t) is equal to the reference amplitude value RMA, and calculates the correction amount using the expressions (5), (6), and (7) (see the first embodiment).

The above process is also performed on the frequency bands (2) and (3). The correction amount is independently calculated for each frequency band, and three correction amounts are output to the texture correction section 360.

The texture correction section 360 is described in detail below with reference to FIG. 16. The texture correction section 360 includes a process parameter control section 1368, multiplication sections 1361, 1362, and 1263, upsampling sections 1364 and 1366, and summation sections 1365 and 1367.

The flow of data transferred between these sections is described below. The process parameter control section 1368 outputs the reduction ratio that corresponds to the frequency bandwidth divided based on the magnification information output from the control section 302 and applied by the texture extraction section 320 to the upsampling sections 1364 and 1366.

The multiplication section 1361 receives the sub-band image that is output from the texture extraction section 320 and corresponds to the frequency band (3) in FIG. 14A or 14B and the correction amount that is output from the texture correction amount calculation section 340 and corresponds to the sub-band image that corresponds to the frequency band (3), multiplies the correction amount by the sub-band image that corresponds to the frequency band (3) to generate a corrected sub-band image that corresponds to the frequency band (3), and outputs the corrected sub-band image to the upsampling section 1364.

The multiplication section 1362 receives the sub-band image that is output from the texture extraction section 320 and corresponds to the frequency band (2) in FIG. 14A or 14B and the correction amount that is output from the texture correction amount calculation section 340 and corresponds to the sub-band image that corresponds to the frequency band (2), multiplies the correction amount by the sub-band image that corresponds to the frequency band (2) to generate a corrected sub-band image that corresponds to the frequency band (2), and outputs the corrected sub-band image to the summation section 1365.

The multiplication section 1363 receives the sub-band image that is output from the texture extraction section 320 and corresponds to the frequency band (1) in FIG. 14A or 14B and the correction amount that is output from the texture correction amount calculation section 340 and corresponds to the sub-band image that corresponds to the frequency band (1), multiplies the correction amount by the sub-band image that corresponds to the frequency band (1) to generate a corrected sub-band image that corresponds to the frequency band (1), and outputs the corrected sub-band image to the summation section 1367.

The upsampling section 1364 receives the corrected sub-band image that is output from the multiplication section 1364 and corresponds to the frequency band (3) and the reduction ratio that is output from the process parameter control section 1368 and corresponds to the frequency band (3), magnifies the corrected sub-band image that corresponds to the frequency band (3) at a magnification that is a reciprocal of the reduction ratio to generate a magnified corrected sub-band image that corresponds to the frequency band (3), and outputs the magnified corrected sub-band image to the summation section 1365.

The summation section 1365 receives the magnified corrected sub-band image that is magnified by the upsampling section 1364 and corresponds to the frequency band (3) and the sub-band image that is output from the multiplication section 1362 and corresponds to the frequency band (2), sums the sub-band images to generate a corrected sub-band image that corresponds to the frequency band ((3)+(2)), and outputs the corrected sub-band image to the upsampling section 1366.

The upsampling section 1366 receives the corrected sub-band image that is output from the summation section 1365 and corresponds to the frequency band ((3)+(2)) and the reduction ratio that is output from the process parameter control section 1368 and corresponds to the frequency band (2), magnifies the corrected sub-band image that corresponds to the frequency band ((3)+(2)) at a magnification that is a reciprocal of the reduction ratio that corresponds to the frequency band (2) to generate a magnified corrected sub-band image that corresponds to the frequency band ((3)+(2)), and outputs the magnified corrected sub-band image to the summation section 1367.

The summation section 1367 receives the magnified corrected sub-band image that is magnified by the upsampling section 1366 and corresponds to the frequency band ((3)+(2)) and the corrected sub-band image that is output from the multiplication section 1363 and corresponds to the frequency band (1), sums the sub-band images to generate a corrected sub-band image that corresponds to the frequency band ((3)+(2)+(1)), and outputs the corrected sub-band image to the blending section 370.

The subsequent process is the same as described above in connection with the first embodiment.

3.4 Details of Autofocus Process

Figure 17:
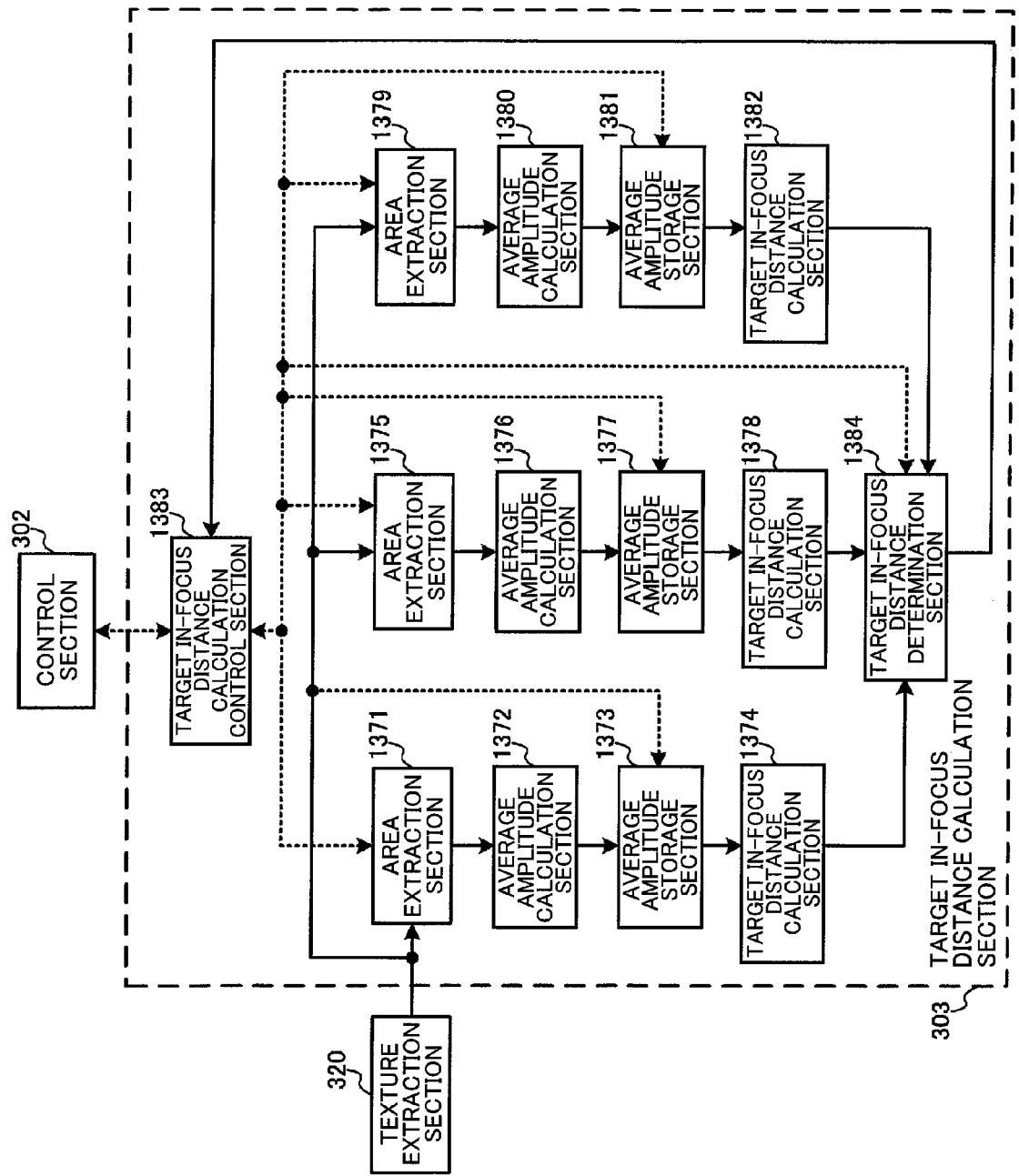
FIG. 17 illustrates a configuration example of a target in-focus distance calculation section.

The target in-focus distance calculation section 303 is described in detail below with reference to FIG. 17. The target in-focus distance calculation section 303 includes area extraction sections 1371, 1375, and 1379, average amplitude calculation sections 1372, 1376, and 1380, average amplitude storage sections 1373, 1377, and 1381, target in-focus distance calculation sections 1374, 1378, and 1382, a target in-focus distance determination section 1384, and a target in-focus distance calculation control section 1383.

The target in-focus distance calculation section 303 is configured to utilize a contrast method. Therefore, it is necessary to set a contrast detection area. For example, target in-focus distance information (e.g., an identification number of an area selected from a plurality of rectangular areas set in advance) that is designated by the user is input to the control section 302 from the external I/F section 500, and converted into contrast detection area information (i.e., coordinates of the rectangular area within the time-series display image) by the control section 302.

The flow of data transferred between the above sections is described below. The target in-focus distance calculation control section 1383 receives the contrast detection area information and the magnification information output from the control section 302 and the current in-focus distance set in the in-focus distance control section 206. The target in-focus distance calculation control section 1383 calculates contrast detection area coordinates that correspond to three sub-band images output from the texture extraction section 320 based on the contrast detection area information and the magnification information, and outputs the calculated contrast detection area coordinates to the area extraction sections 1371, 1375, and 1379. The current in-focus distance is output to the average amplitude storage sections 1373, 1377, and 1381. The contrast detection area coordinates are calculated as described below. The coordinates output from the control section 302 are used directly for the frequency band (1). The coordinates for the frequency band (1) are reduced by the reduction ratio that is output from the process parameter control section 1368 and corresponds to the frequency band (2) to calculate coordinates for the frequency band (2). The coordinates for the frequency band (2) are reduced by the reduction ratio that is output from the process parameter control section 1368 and corresponds to the frequency band (3) to calculate coordinates for the frequency band (3).

The area extraction sections 1371, 1375, and 1379 extract the contrast detection area from three sub-band images output from the texture extraction section 320 based on the contrast detection area coordinates output from the target in-focus distance calculation control section 1383, and output the contrast detection area to the average amplitude calculation sections 1372, 1376, and 1380, respectively.

The average amplitude calculation sections 1372, 1376, and 1380 calculate the average value of the absolute value of the pixel value within the contrast detection area extracted from each sub-band image output from the area extraction sections 1371, 1375, and 1379 as an average amplitude value, and output the average amplitude value to the average amplitude storage sections 1373, 1377, and 1381, respectively.

The average amplitude storage sections 1373, 1377, and 1381 (ring buffer) store at least nine in-focus distances that correspond to the average amplitude values calculated in time series, and necessarily store the average amplitude value output from the average amplitude calculation section 1372, 1376, or 1380 and the in-focus distance output from the target in-focus distance calculation control section 1383 as the latest average amplitude value and the latest in-focus distance.

The target in-focus distance calculation sections 1374, 1378, and 1382 read three average amplitude values (every three average amplitude values among the nine average amplitude values and the latest average amplitude value) and the in-focus distances that correspond to the three average amplitude values from the average amplitude storage sections 1373, 1377, and 1381 (ring buffer), and calculate the target in-focus distance that corresponds to the maximum amplitude value using a Lagrange interpolation process or the like. The calculated target in-focus distances are output to the target in-focus distance determination section 1384 together with the corresponding maximum amplitude values.

The target in-focus distance determination section 1384 receives the target in-focus distances that are output from the target in-focus distance calculation sections 1374, 1378, and 1382 and correspond to the three sub-band images and the calculated three maximum amplitude values. The target in-focus distance determination section 1384 selects the largest amplitude value from the three maximum amplitude values, and outputs the target in-focus distance that corresponds to the selected amplitude value to the target in-focus distance calculation control section 1383 as the actual target in-focus distance. The target in-focus distance may be determined while reducing the effects of noise by calculating a weighted average of the target in-focus distances using the corresponding maximum amplitude values as weights, and determining the calculated weighted average as the actual target in-focus distance.

The target in-focus distance calculation control section 1383 outputs the target in-focus distance input from the target in-focus distance determination section 1384 to the control section 302.

The control section 302 outputs the target in-focus distance to the in-focus distance control section 206 to move the in-focus distance adjustment lens 207 to the target in-focus distance.

According to the second embodiment, since the autofocus process performed during zoom observation of the endoscope apparatus having a low frame rate can be controlled using the contrast value based on the texture extracted corresponding to the observation target, the in-focus accuracy can be improved. Moreover, since it is possible to suppress a temporal change in defocus amount that occurs due to wobbling in the direction Z during the autofocus process, the user can closely examine a lesion area within a short time without stress, and the burden imposed on the patient can be reduced.

According to the second embodiment, the specific frequency band image extraction section may include a frequency band separation section that generates a plurality of sub-band images, and a sub-band selection section that selects one or more sub-band images from the plurality of sub-band images to generate the specific frequency band image.

Figure 12:
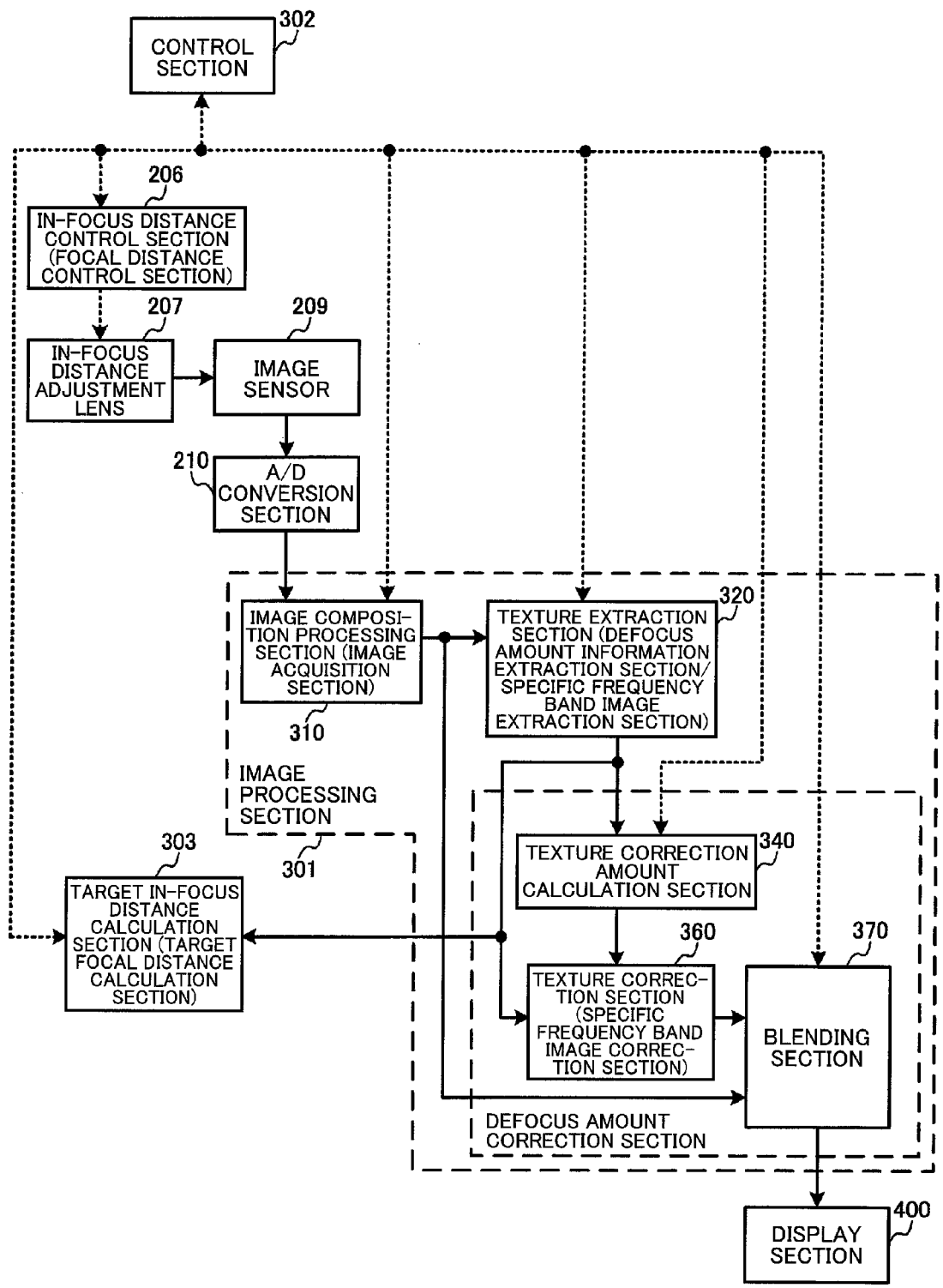
FIG. 12 illustrates another configuration example of an image processing section.

The term "sub-band image" used herein refers to an image obtained by dividing (separating) the captured image into a plurality of specific frequency bands determined based on the magnification information. In the examples illustrated in FIGS. 14A and 14B, (1) to (4) indicate the sub-band images. The frequency band separation section corresponds to the texture extraction section 320 illustrated in FIG. 12, and the sub-band selection section corresponds to the texture correction amount calculation section 340 and the like illustrated in FIG. 12.

This makes it possible to extract the specific frequency band image based on the sub-band image. More specifically, the captured image is divided into a plurality of sub-band images, and an appropriate sub-band image is selected from the sub-band images to generate the specific frequency band image. It is possible to implement a control process corresponding to the magnification (corresponding the control process illustrated in FIG. 19 in the first embodiment) by changing the width of the sub-band image corresponding to the imaging magnification of the optical system (see FIGS. 14A and 14B).

The correction amount multiplication section may include a sub-band image correction amount multiplication section that calculates the correction amount corresponding to each sub-band image based on the amplitude value that is calculated by the specific frequency band image amplitude calculation section and corresponds to each sub-band image and the magnification information about the optical system.

Figure 16:
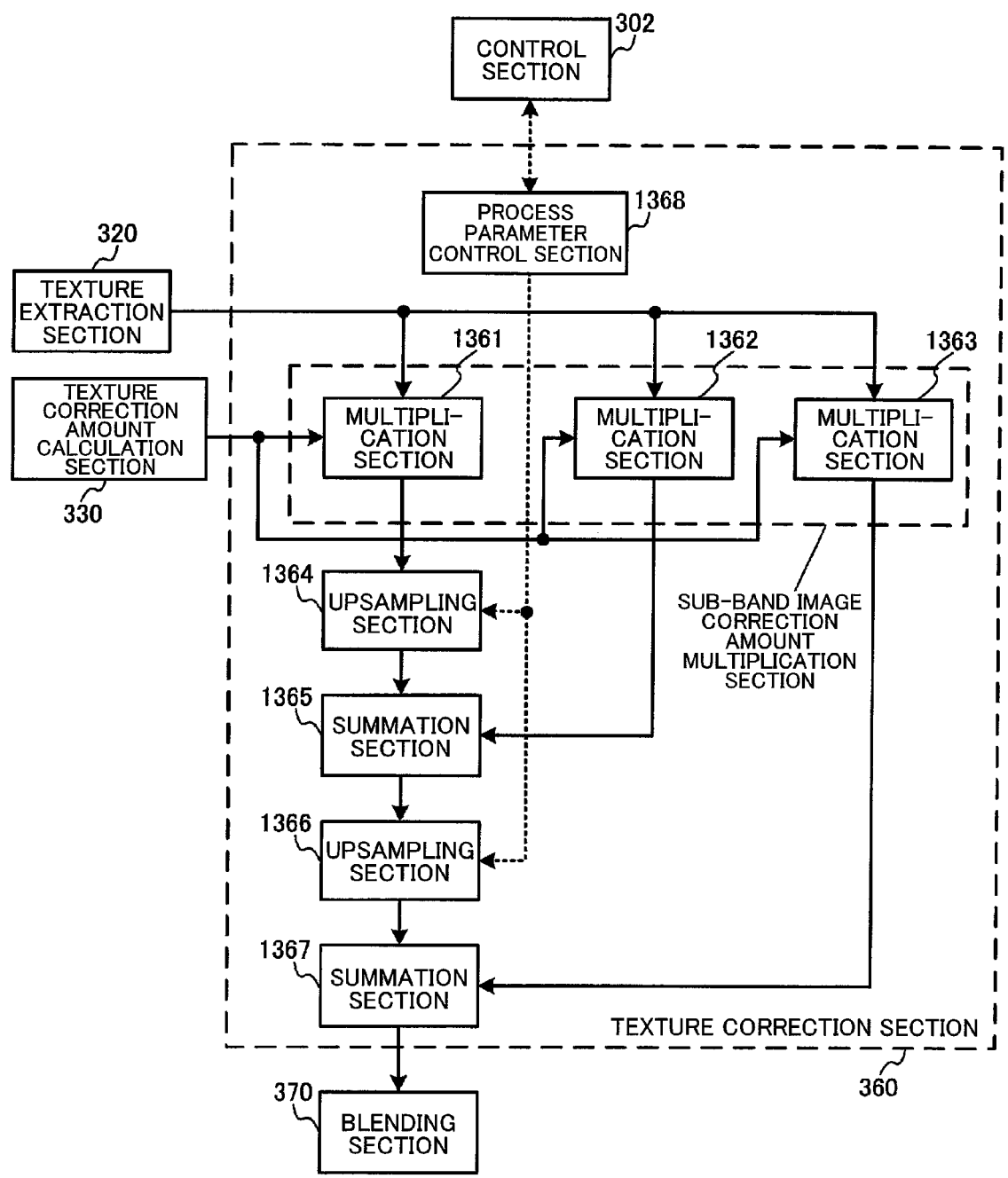
FIG. 16 illustrates a configuration example of a texture correction section.

The sub-band image correction amount multiplication section corresponds to the multiplication sections 1361 to 1363 illustrated in FIG. 16.

According to the above configuration, the specific frequency band image can be corrected by multiplying each sub-band image by the correction amount. More specifically, the correction process is performed so that the amplitude value of the correction target image is equal to the reference amplitude value in the same manner as in the first embodiment. In the second embodiment, it is possible to deal with the control process corresponding to the amplitude by providing a bright spot removal process that utilizes a process that removes a steep edge that changes with the passage of time before dividing the captured image into the sub-band images. Note that the process that removes a steep edge that changes with the passage of time may be a process that determines the brightness level based on a threshold value that is set based on the image average value, and a determination area deletion process (e.g., morphological process), for example. A plurality of sub-band images may be selected, and only the selected sub-band images may be multiplied by the correction amount. Alternatively, each sub-band image may be multiplied by the correction amount, and an unnecessary sub-band image may be multiplied by 0. The latter configuration is employed in FIGS. 13 and 16 (block diagrams).

The optical system of the endoscope apparatus may include a focal distance control section that controls a focal distance, and a target focal distance calculation section that calculates a target focal distance based on the defocus amount of the captured image. The focal distance control section may control the focal distance based on the target focal distance calculated by the target focal distance calculation section.

The defocus amount information about the captured image is calculated by the defocus amount information extraction section for a plurality of captured images at a plurality of focal distances. The focal distance control section corresponds to the in-focus distance control section 206 illustrated in FIG. 12, and the target focal distance calculation section corresponds to the target in-focus distance calculation section 303 illustrated in FIG. 12.

The above configuration makes it possible to implement an autofocus process. Note that the image may be outside the depth of field since the autofocus process is based on the contrast method that moves the lens to achieve a plurality of focal distances, and calculates the target in-focus distance (see FIG. 11). Therefore, the defocus restoration process implemented by image processing is necessary. Since an in-focus state and a defocused state occur within a short time, the defocus restoration process implemented by image processing is important when the frame rate is low in order to provide an image that does not produce a wrong impression to the user.

The defocus amount correction section may determine the captured image acquired at a focal distance that has been determined to be in focus by the focal distance control section to be the in-focus captured image. The defocus amount correction section may perform the correction process based on the defocus amount information about the in-focus captured image.

This makes it possible to use an image acquired at a focal distance that has been determined to be in focus during the autofocus process as the in-focus captured image that is used as a reference for calculating the correction amount. Therefore, the reference amplitude value update process using the autofocus process is performed in addition to the reference amplitude value update process described above in connection with the first embodiment, and the reference amplitude value can be accurately updated.

The first and second embodiments according to the invention and the modifications thereof have been described above. Note that the invention is not limited to the first and second embodiments and the modifications thereof. Various modifications and variations may be made without departing from the scope of the invention. A plurality of elements disclosed in connection with the first and second embodiments and the modifications thereof may be appropriately combined to implement various configurations. For example, an arbitrary element may be omitted from the elements described in connection with the first and second embodiments and the modifications thereof. Some of the elements disclosed in connection with different embodiments or modifications thereof may be appropriately combined. Specifically, various modifications and applications are possible without materially departing from the novel teachings and advantages of the invention.

What is claimed is:

1. An endoscope apparatus comprising:
   an image acquisition section that acquires a captured image in a zoom observation state in time series based on an image signal from an image sensor, the zoom observation state being an observation state in which a magnification of an optical system is higher than that in a normal observation state;
   a defocus amount information extraction section that extracts defocus amount information from the captured image in the zoom observation state; and
   a defocus amount correction section that corrects the captured image based on the extracted defocus amount information,
   wherein the defocus amount information extraction section includes a specific frequency band image extraction section that extracts, as the defocus amount information, a specific frequency band image from the captured image, the specific frequency band image being an image of a specific frequency band which is determined in accordance with the magnification of the optical system in the zoom observation state,
   wherein:
   the specific frequency band image extraction section includes:
      an extraction condition control section that controls an extraction condition for the specific frequency band image based on magnification information about the optical system of the endoscope apparatus, such that the specific frequency band of the specific frequency band image is changed according to the magnification;
      a filtering section which performs a filter process based on the extraction condition to obtain a filtered image;
      a subtraction section which generates an image by subtracting the filtered image from the captured image which has not been subjected to the filter process; and
      a noise amount estimation section which estimates a noise amount based on the extraction condition;
   the specific frequency band image extraction section extracts the specific frequency band image based on the image generated by the subtraction section and the noise amount estimated by the noise amount estimation section; and
   the defocus amount correction section includes:
      a specific frequency band image amplitude calculation section that calculates an amplitude value of the specific frequency band image extracted by the specific frequency band image extraction section based on a pixel value of the specific frequency band image;
      a specific frequency band image correction section that corrects the amplitude value of the specific frequency band image to match a correction target value corresponding to an in-focus amplitude value of the specific frequency band image; and
      a blending section that blends the captured image and the corrected specific frequency band image to thereby correct the captured image and obtain a corrected captured image that is in focus.

2. The endoscope apparatus as defined in claim 1, wherein the specific frequency band image extraction section further includes a captured image amplitude calculation section that calculates an amplitude value of the captured image,
   wherein the specific frequency band image extraction section extracts the specific frequency band image based further on the amplitude value of the captured image calculated by the captured image amplitude calculation section such that (i) the specific frequency band image extraction section does not extract the specific frequency band image when the amplitude value calculated by the captured image amplitude calculation section is within a first amplitude range, (ii) the specific frequency band image extraction section extracts the specific frequency band image when the amplitude value calculated by the captured image amplitude calculation section is within a second amplitude range, the second amplitude range being a range that corresponds to an amplitude value that is smaller than an amplitude value within the first amplitude range, and (iii) the specific frequency band image extraction section does not extract the specific frequency band image when the amplitude value calculated by the captured image amplitude calculation section is within a third amplitude range, the third amplitude range being a range that corresponds to an amplitude value that is smaller than an amplitude value within the second amplitude range.

3. The endoscope apparatus as defined in claim 2, wherein the specific frequency band image, of which the amplitude value calculated by the captured image amplitude calculation section is within the second amplitude range, is an image that corresponds to a surface of a mucous membrane and a blood vessel in a surface of tissue.

4. The endoscope apparatus as defined in claim 2, wherein an image of which the amplitude value calculated by the captured image amplitude calculation section is within the first amplitude range is an image that corresponds to folds on a surface of tissue, and an image of which the amplitude value calculated by the captured image amplitude calculation section is within the third amplitude range is an image that corresponds to noise.

5. The endoscope apparatus as defined in claim 1, wherein the specific frequency band image extraction section includes a captured image amplitude calculation section that calculates an amplitude value of the captured image,
   wherein the specific frequency band image extraction section extracts the specific frequency band image based further on the amplitude value of the captured image calculated by the captured image amplitude calculation section such that (i) the specific frequency band image extraction section does not extract the specific frequency band image when the amplitude value calculated by the captured image amplitude calculation section is within a first amplitude range, and (ii) the specific frequency band image extraction section extracts the specific frequency band image when the amplitude value calculated by the captured image amplitude calculation section is within a second amplitude range, the second amplitude range being a range that corresponds to an amplitude value that is smaller than an amplitude value within the first amplitude range, wherein the specific frequency band image is an image of which the amplitude value calculated by the captured image amplitude calculation section is within the second amplitude range and the frequency band is within a first frequency range, the first frequency range being a range that corresponds to a frequency that is higher than a frequency within a second frequency range and is determined based on the magnification information.

6. The endoscope apparatus as defined in claim 1, wherein the specific frequency band of the specific frequency band image is within a first frequency range, and a frequency within the first frequency range is higher than a frequency within a second frequency range, the first frequency range being a range that is larger than a first frequency threshold value and smaller than a second frequency threshold value, and wherein the specific frequency band image extraction section increases the first frequency threshold value and the second frequency threshold value as the magnification indicated by the magnification information about the optical system of the endoscope apparatus increases.

7. The endoscope apparatus as defined in claim 1, wherein the specific frequency band image extraction section includes:
   a frequency band separation section that generates a plurality of sub-band images, the sub-band image being an image obtained by dividing the captured image into a plurality of specific frequency bands determined based on the magnification information; and
   a sub-band selection section that selects one or more sub-band images from the plurality of sub-band images to generate the specific frequency band image.

8. The endoscope apparatus as defined in claim 1, wherein:
   the filtering section comprises a first filtering section which performs a first filter process as the filter process; and
   the specific frequency band image extraction section further includes:
      a second filtering section;
   the image generated by the subtraction section is a structural image, and the subtraction section calculates a difference between the filtered image obtained by the first filter process performed by the first filtering section and the captured image to generate the structural image,
   the noise amount estimation section estimates a noise amount of the structural image based on the extraction condition, and
   the second filtering section separates noise from the structural image based on the noise amount estimated by the noise amount estimation section to acquire the specific frequency band image.

9. The endoscope apparatus as defined in claim 8, wherein the specific frequency band image extraction section includes a captured image amplitude calculation section that calculates an amplitude value of the captured image,
wherein the specific frequency band image extraction section extracts the specific frequency band image based further on the amplitude value of the captured image calculated by the captured image amplitude calculation section such that (i) the specific frequency band image extraction section does not extract the specific frequency band image when the amplitude value calculated by the captured image amplitude calculation section is within a first amplitude range, and (ii) the specific frequency band image extraction section extracts the specific frequency band image when the amplitude value calculated by the captured image amplitude calculation section is within a second amplitude range, the second amplitude range being a range that corresponds to an amplitude value that is smaller than an amplitude value within the first amplitude range, and
wherein the first filtering section subjects an image within the first amplitude range to a low-pass filter process that allows a frequency band that corresponds to a first frequency range and a second frequency range to pass through, the first frequency range being a range that corresponds to a frequency that is higher than a frequency within a second frequency range, and subjects an image within the second amplitude range to a low-pass filter process that allows a frequency band that corresponds to the second frequency range to pass through, and blocks a frequency band that corresponds to the first frequency range.

10. The endoscope apparatus as defined in claim 8, wherein the first filtering section includes:
   an area extraction section that extracts a given area around an attention pixel from the captured image;
   a filter coefficient calculation section that calculates a spatial distance and a difference in pixel value between the attention pixel and a peripheral pixel within the given area, and calculates a filter coefficient for a pixel within each given area based on the extraction condition; and
   a filtering section that performs the first filter process using the given area and the filter coefficient.

11. The endoscope apparatus as defined in claim 8,
wherein the specific frequency band image extraction section includes a captured image amplitude calculation section that calculates an amplitude value of the captured image,
wherein the specific frequency band image extraction section extracts the specific frequency band image based further on the amplitude value of the captured image calculated by the captured image amplitude calculation section such that (i) the specific frequency band image extraction section does not extract the specific frequency band image when the amplitude value calculated by the captured image amplitude calculation section is within a first amplitude range, and (ii) the specific frequency band image extraction section extracts the specific frequency band image when the amplitude value calculated by the captured image amplitude calculation section is within a second amplitude range, the second amplitude range being a range that corresponds to an amplitude value that is smaller than an amplitude value within the first amplitude range, and wherein the second filtering section subjects an image within the second amplitude range to a low-pass filter process that allows a frequency band that corresponds to a first frequency range and a second frequency range to pass through, the first frequency range being a range that corresponds to a frequency that is higher than a frequency within a second frequency range, and subjects an image within a third amplitude range that is higher than the second amplitude range to a low-pass filter process that allows a frequency band that corresponds to the second frequency range to pass through, and blocks a frequency band that corresponds to the first frequency range.

12. The endoscope apparatus as defined in claim 8, wherein the second filtering section includes:
an area extraction section that extracts a given area around an attention pixel from the structural image;
a filter coefficient calculation section that calculates a spatial distance and a difference in pixel value between the attention pixel and a peripheral pixel within the given area, and calculates a filter coefficient for a pixel within each given area based on the noise amount; and
a noise separation section that performs a filter process using the extracted area and the filter coefficient to separate noise from the attention pixel.

13. The endoscope apparatus as defined in claim 1, wherein the defocus amount correction section corrects the captured image acquired in time series based on a defocus amount of an in-focus captured image which is a captured image that has been determined to be in focus.

14. The endoscope apparatus as defined in claim 13, wherein the in-focus captured image is a captured image extracted when the optical system of the endoscope apparatus has been switched to the zoom observation state.

15. The endoscope apparatus as defined in claim 13, wherein the in-focus captured image is a captured image that has been extracted after the optical system of the endoscope apparatus has been switched to the zoom observation state, and has an amplitude value of the specific frequency band image that has satisfied a given condition within a given period.

16. The endoscope apparatus as defined in claim 15, wherein the in-focus captured image is a captured image that has been extracted after the optical system of the endoscope apparatus has been switched to the zoom observation state, and has an amplitude value of the specific frequency band image that is larger than a reference amplitude determination threshold value and has a maximum value.

17. The endoscope apparatus as defined in claim 1, wherein the specific frequency band image correction section includes:
a reference amplitude value selection section that selects the in-focus amplitude value that has been determined to be in focus from the amplitude value of the specific frequency band image calculated in time series by the specific frequency band image amplitude calculation section as a reference amplitude value corresponding to the correction target value; and
a correction amount multiplication section that calculates a correction amount for the specific frequency band image based on the reference amplitude value, and multiplies the specific frequency band image by the correction amount.

18. The endoscope apparatus as defined in claim 17, wherein:
the specific frequency band image extracted by the specific frequency band image extraction section is one or more sub-band images having one or more frequency bands, and
the correction amount multiplication section includes a sub-band image correction amount multiplication section that calculates the correction amount corresponding to each sub-band image based on one or more amplitude values that are calculated by the specific frequency band image amplitude calculation section and correspond to each sub-band image and the magnification information about the optical system of the endoscope apparatus, and multiplies each sub-band image by the calculated correction amount.

19. The endoscope apparatus as defined in claim 1, further comprising:
a focal distance control section that controls a focal distance; and
a target focal distance calculation section that calculates a target focal distance based on the defocus amount information calculated by the defocus amount information extraction section for the captured images based on a plurality of focal distances moved in time series by the focal distance control section, the focal distance control section controlling the focal distance based on the target focal distance.

20. The endoscope apparatus as defined in claim 19, wherein the defocus amount correction section determines the captured image acquired at a focal distance that has been determined to be in focus by the focal distance control section to be an in-focus captured image, and corrects the captured image based on the defocus amount information about the in-focus captured image.

21. The endoscope apparatus as defined in claim 1, wherein the zoom observation state is a state in which the magnification of the optical system of the endoscope apparatus is equal to or higher than a given magnification.

22. The endoscope apparatus as defined in claim 1,
wherein the specific frequency band image extraction section further includes a captured image amplitude calculation section that calculates an amplitude value of the captured image, and
wherein the specific frequency band image extraction section extracts the specific frequency band image based further on the amplitude value of the captured image calculated by the captured image amplitude calculation section such that (i) the specific frequency band image extraction section does not extract the specific frequency band image when the amplitude value calculated by the captured image amplitude calculation section is within a first amplitude range, and (ii) the specific frequency band image extraction section extracts the specific frequency band image when the amplitude value calculated by the captured image amplitude calculation section is within a second amplitude range, the second amplitude range being a range that corresponds to an amplitude value that is smaller than an amplitude value within the first amplitude range.

23. An information storage device storing a program that instructs a computer to perform functions comprising:
acquiring a captured image in a zoom observation state in time series, the zoom observation state being an observation state in which a magnification of an optical system is higher than that in a normal observation state;

performing a defocus amount information extraction process that extracts defocus amount information from the captured image in the zoom observation state; and performing a defocus amount correction process that corrects the captured image based on the extracted defocus amount information, wherein:

the defocus amount information extraction process comprises performing a specific frequency band image extraction process of extracting, as the defocus amount information, a specific frequency band image from the captured image, the specific frequency band image being an image of a specific frequency band which is determined in accordance with the magnification of the optical system in the zoom observation state, the specific frequency band image extraction process includes:

an extraction condition control process that controls an extraction condition for the specific frequency band image based on magnification information about the optical system of the endoscope apparatus, such that the specific frequency band of the specific frequency band image is changed according to the magnification;

a filter process which is performed based on the extraction condition to obtain a filtered image;

a subtraction process that generates an image by subtracting the filtered image from the captured image which has not been subjected to the filter process; and a noise amount estimation process that estimates a noise amount based on the extraction condition;

the specific frequency band image extraction process extracts the specific frequency band image based on the image generated by the subtraction process and the noise amount estimated by the noise amount estimation process, and the defocus amount correction process includes:

a specific frequency band image amplitude calculation process that calculates an amplitude value of the specific frequency band image extracted by the specific frequency band image extraction process based on a pixel value of the specific frequency band image;

a specific frequency band image correction process that corrects the amplitude value of the specific frequency band image to match a correction target value corresponding to an in-focus amplitude value of the specific frequency band image; and a blending process that blends the captured image and the corrected specific frequency band image to thereby correct the captured image and obtain a corrected captured image that is in focus.

24. The information storage device as defined in claim 23, wherein the specific frequency band image extraction process further includes a captured image amplitude calculation process that calculates an amplitude value of the captured image, and wherein the specific frequency band image extraction process extracts the specific frequency band image based further on the amplitude value of the captured image calculated by the captured image amplitude calculation process such that (i) the specific frequency band image extraction process does not extract the specific frequency band image when the amplitude value calculated by the captured image amplitude calculation process is within a first amplitude range, and (ii) the specific frequency band image extraction process extracts the specific frequency band image when the amplitude value calculated by the captured image amplitude calculation process is within a second amplitude range, the second amplitude range being a range that corresponds to an amplitude value that is smaller than an amplitude value within the first amplitude range.

25. An image processing method for an image processing apparatus, the method comprising, with the image processing apparatus:

acquiring a captured image in a zoom observation state in time series, the zoom observation state being an observation state in which a magnification of an optical system is higher than that in a normal observation state;

performing a defocus amount information extraction process that extracts defocus amount information from the captured image in the zoom observation state; and performing a defocus amount correction process that corrects the captured image based on the extracted defocus amount information, wherein:

the defocus amount information extraction process comprises performing a specific frequency band image extraction process of extracting, as the defocus amount information, a specific frequency band image from the captured image, the specific frequency band image being an image of a specific frequency band which is determined in accordance with the magnification of the optical system in the zoom observation state, the specific frequency band image extraction process includes:

an extraction condition control process that controls an extraction condition for the specific frequency band image based on magnification information about the optical system of the endoscope apparatus, such that the specific frequency band of the specific frequency band image is changed according to the magnification;

a filter process which is performed based on the extraction condition to obtain a filtered image;

a subtraction process that generates an image by subtracting the filtered image from the captured image which has not been subjected to the filter process; and a noise amount estimation process that estimates a noise amount based on the extraction condition;

the specific frequency band image extraction process extracts the specific frequency band image based on the image generated by the subtraction process and the noise amount estimated by the noise amount estimation process, and the defocus amount correction process includes:

a specific frequency band image amplitude calculation process that calculates an amplitude value of the specific frequency band image extracted by the specific frequency band image extraction process based on a pixel value of the specific frequency band image;

a specific frequency band image correction process that corrects the amplitude value of the specific frequency band image to match a correction target value corresponding to an in-focus amplitude value of the specific frequency band image; and a blending process that blends the captured image and the corrected specific frequency band image to thereby correct the captured image and obtain a corrected captured image that is in focus.

26. The image processing method as defined in claim 25, wherein the specific frequency band image extraction process further includes a captured image amplitude calculation process that calculates an amplitude value of the captured image, and wherein the specific frequency band image extraction process extracts the specific frequency band image based further on the amplitude value of the captured image calculated by the captured image amplitude calculation process such that (i) the specific frequency band image extraction process does not extract the specific frequency band image when the amplitude value calculated by the captured image amplitude calculation process is within a first amplitude range, and (ii) the specific frequency band image extraction process extracts the specific frequency band image when the amplitude value calculated by the captured image amplitude calculation process is within a second amplitude range, the second amplitude range being a range that corresponds to an amplitude value that is smaller than an amplitude value within the first amplitude range.

* * * * *